US006852710B2

(12) United States Patent
Rao et al.

(10) Patent No.: US 6,852,710 B2
(45) Date of Patent: Feb. 8, 2005

(54) 2-ALKOXYESTRADIOL ANALOGS WITH ANTIPROLIFERATIVE AND ANTIMITOTIC ACTIVITY

(75) Inventors: Pemmaraju Narasimha Rao, San Antonio, TX (US); Susan L. Mooberry, San Antonio, TX (US); James W. Cessac, San Antonio, TX (US); Tina L. Tinley, Kerrville, TX (US)

(73) Assignee: Southwest Foundation for Biomedical Research, San Antonio, TX (US)

( * ) Notice: Subject to any disclaimer, the term of this patent is extended or adjusted under 35 U.S.C. 154(b) by 0 days.

(21) Appl. No.: 10/412,007

(22) Filed: Apr. 11, 2003

(65) Prior Publication Data

US 2003/0229061 A1 Dec. 11, 2003

Related U.S. Application Data

(62) Division of application No. 10/167,208, filed on Jun. 11, 2002, now Pat. No. 6,593,321.
(60) Provisional application No. 60/297,428, filed on Jun. 11, 2001.

(51) Int. Cl.$^7$ .......................... A61K 31/56; C07J 41/00; C07J 1/00
(52) U.S. Cl. ...................... 514/182; 514/177; 514/178; 514/180; 552/614; 552/518; 552/519
(58) Field of Search ................ 514/182, 178, 514/177, 180, 179; 552/518, 614, 519, 627

(56) References Cited

U.S. PATENT DOCUMENTS

| | | | |
|---|---|---|---|
| 5,504,074 A | 4/1996 | D'Amato et al. | 514/182 |
| 5,661,143 A | 8/1997 | D'Amato et al. | 514/182 |
| 5,892,069 A | 4/1999 | D'Amato et al. | 552/627 |
| 6,051,726 A | 4/2000 | Sachdeva et al. | 552/614 |
| 6,054,598 A | 4/2000 | Sachdeva et al. | 552/627 |
| 6,136,992 A | 10/2000 | Ram et al. | 552/614 |
| 6,162,930 A | 12/2000 | Pinney et al. | 549/57 |
| 6,414,015 B1 | 7/2002 | Mooberry et al. | 514/455 |
| 6,593,321 B2 * | 7/2003 | Rao et al. | 514/182 |

FOREIGN PATENT DOCUMENTS

| | | | |
|---|---|---|---|
| WO | WO 95/04535 | 2/1995 | A61K/31/56 |
| WO | WO 98/40398 | 9/1998 | C07J/1/00 |

OTHER PUBLICATIONS

Breuer, H.; Knuppen, R. Biosynthesis of 2–Methoxyestradiol in Human Liver. *Naturwissenschaften* 1960, 12, 280–281.

Seegers, J. C.; Aveling, M.–L.; van Aswegan, C. H.; Cross, M.; Koch, F.; Joubert, W.S. The Cytotoxic Effects of Estradiol–17β, Catacholestradiols and Methoxyestradiols on Dividing MCF–7 and HeLa Cells. *J. Steroid Biochem.* 1989, 32, 797–809.

Fotsis, T.; Zhang, Y.; Pepper, M. S.; Adlercreutz, H.; Montesano, R.; Nawroth, P. P.; Schweigerer, L. The endogenous oestrogen metabolite 2–methoxyestradiol inhibits angiogenesis and suppresses tumor growth. *Nature* 1994, 368, 237–239.

Cushman, M.; He, H.–M.; Katzenellenbogen, J. A.; Lin, C. M.; Hamel, E. Synthesis, Antitubulin and Antimitotic Activity, and Cytotoxicity of Analogs of 2–Methoxyestradiol, an Endogenous Mammalian Metabolite of Estradiol That Inhibits Tubulin Polymerization by Binding to the Colchicine Binding Site. *J. Med. Chem.* 1995, 38, 2041–2049.

Cushman, M.; He, H.–M.; Katzenellenbogen, J. A.; Varma, R. K.; Hamel, E.; Lin, C. M.; Ram, S. Sachdeva, Y. P. Synthesis of Analogs of 2–Methoxyestradiol with Enhanced Inhibitory Effects on Tubulin Polymerization and Cancer Cell Growth. *J. Med. Chem.* 1997, 40, 2323–2334.

Axelrod, L. R.; Rao, P. N. Synthesis of 2–Hydroxyestradiol–17β. *Chem. Ind.* 1959, 1454–1455.

Axelrod, L. R.; Rao, P. N.; Goldzieher, J. W. The Conversion of 2–Hydroxyestradiol–17 β to 2–Hydroxy and 2–Methoxy Metabolites in Human Urine. *Arch. Biochem. Biophys.* 1961, 94, 265–268.

Rao, P. N.; Axelrod, L. R. 2–Hydroxy–(Estrogens. Part II. Synthesis of 2,3–Dihydroxy–(Estra– 1,3, 5(10)–trien–17–one and (Estra–1,3,5(10)–triene–2,3,16α, 17β –tetraol. *J. Chem. Soc.* 1961, 4769–4773.

Rao, P. N.; Jacob, E. J.; Axelrod, L. R. Total Synthesis of Polymethoxyoestrane Compounds. Part I. Synthesis of (±)–2,3,4–Trimethoxyoestra–1,3,5(10)–trien–17β –o1 and Related Compounds. *J. Chem. Soc., Sect C.* 1971, 2855–2860.

Rao, P. N.; Axelrod, L. R. Total Synthesis of Polymethoxyoestrane Compounds. Part II. Synthesis of (±)–2, 4–Dimethoxyoestra–1,3,5(10)–trien–17β–o1. *J. Chem. Soc., Sect C.* 1971, 2861–2863.

(List continued on next page.)

Primary Examiner—Sabiha N. Qazi
(74) Attorney, Agent, or Firm—Cox Smith Matthews Incorporated

(57) ABSTRACT

The application discloses novel 2-alkoxyestradiol analogs which exhibit anti-proliferative properties, and methods of making and using such compounds to inhibit undesired cell proliferation and tumor growth. Additionally, methods are disclosed of treating diseases associated with undesired angiogenesis and undesired proliferation, and methods of treating infectious disease wherein the infectious agent is particularly susceptible to inhibition by agents that disrupt microtubule organization and function.

21 Claims, 9 Drawing Sheets

OTHER PUBLICATIONS

Rao, P. N.; Burdett Jr., J. E. A Novel Two–Step Synthesis of 2–Methoxyestradiol. *Synthesis* 1977, 168–169.

Rao, P. N.; Somawardhana, C. W. Synthesis of 2–Methoxy and 4–Methoxy Equine Estrogens. *Steroids 1987, 49, 419–432*.

Skehan, P.; Storeng, R.; Scudiero, D., Monks; A., McMahon, J.; Vistica, D., Warren, J. T.; Bokesch, H.; Kenney, S.; and Boyd, M. R. New Colorimetric Cytotoxicity Assay for Anticancer–Drug Screening. *J. Natl. Cancer Inst. 1990, 82, 1107–1112*.

Harrowven, D. C. Danity, R. F. Zirconium Tetrachloride as a Mediator for Ambient Temperature Ortho–Fries Rearrangements. *Tetrahedron Lett. (1996), 37, 7659–7660*.

Alberts, B. Bray, D., Lewis, J., Raff, M, Roberts, K., Watson, *J. Molecurar Biology of the Cell*, pp. 652–661 (1989).

Stryer, L., *Biochemistry* (1988) pp. 938–947.

* cited by examiner

2-ALKOXYESTRADIOL ANALOGS WITH ANTIPROLIFERATIVE AND ANTIMITOTIC ACTIVITY

This application claims the benefit under Title 35 United States Code §120 and is a division of U.S. patent application Ser. No. 10/167,208 filed Jun. 11, 2002 now U.S. Pat. No. 6,593,321 which further claims the benefit under Title 35 United States Code §119(e) of U.S. Provisional Application No. 60/297,428 filed on Jun. 11, 2001.

BACKGROUND OF THE INVENTION

1. Field of Invention

The present invention relates, in general, to chemical compounds having antiproliferative and antimitotic activity. More specifically, the present invention is directed to novel 2-alkoxy estradiols having antiproliferative and antimitotic activity and to methods of preparing and using these novel compounds.

2. Description of the Related Art

Certain 2-alkoxy estradiols have been discovered to have antitumor activity (U.S. Pat. No. 6,136,992; U.S. Pat. No. 6,054,598; U.S. Pat. No. 6,051,726; U.S. Pat. No. 5,892,069; U.S. Pat. No. 5,661,143; U.S. Pat. No. 5,504,074; WO 95/04535) (all patents cited throughout this specification are incorporated herein by reference). 2-Methoxyestradiol (2-ME2) is one such 2-alkoxy estradiol exhibiting antitumor activity (U.S. Pat. No. 5,892,069; U.S. Pat. No. 5,661,143; U.S. Pat. No. 5,504,074; WO 95/04535) 2-Methoxyestradiol is an endogenous mammalian metabolite formed by the sequential biochemical hydroxylation and methylation of the natural hormone estradiol (Breuer, H. et al., *Naturwissenschaften* 12, pp. 280–281 (1960)).

Recent studies have demonstrated that the mechanism responsible for the antitumor activity exhibited by certain 2-alkoxy estradiols, including 2-ME2, Includes interference with or prevention of cell mitosis, the multi-step process that preceeds cell division and replication (Alberts, B. et al., *The Cell*, pp. 652–661 (1989); Stryer, L., *Biochemistry* (1988)). For example, some 2-alkoxy estradiols have been shown to inhibit the replication of certain cancer cells by interfering with microtubule formation and function (Seegers, J. C. et al., *J. Steroid Biochem.* 32, pp. 797–809 (1989); U.S. Pat. No. 6,136,992; U.S. Pat. No. 6,054,598; U.S. Pat. No. 6,051,726; U.S. Pat. No. 5,892,069; U.S. Pat. No. 5,661,143; U.S. Pat. No. 5,504,074; WO 95/04535). Microtubules facilitate and make possible, among other things, chromosome and organelle movement and segregation during cell mitosis (Stryer, L., *Biochemistry* (1988)). Preventing or interfering with microtubule formation and function leads to mitotic arrest and frequently to apoptosis. In addition to cancer, many diseases are characterized by undesirable cell proliferation, and the value of compounds and methods that prevent such undesirable cell proliferation is of great importance to the treatment of such diseases. Microtubule formation and function is also critical to cell maintenance, locomotion and the movement of specialized cell structures such as cilia and flagella (Stryer, L., *Biochemistry* (1988)).

To function properly, cilia and flagella require proper tubulin polymerization (U.S. Pat. No. 6,162,930). Certain 2-alkoxy estradiols are known to inhibit tubulin polymerization or to cause the formation of tubulin polymer with altered morphology and stability properties (U.S. Pat. No. 6,136,992). By interfering with normal microtubule dynamics, such compositions may be used to treat those diseases characterized by abnormal proliferation.

Certain 2-alkoxy estradiols, including 2-ME2, have also been demonstrated to act as antiangiogenic agents (Fotsis et al., *Nature* 368, pp. 237–239 (1994); U.S. Pat. No. 6,136,992; U.S. Pat. No. 6,054,598; U.S. Pat. No. 6,051,726; U.S. Pat. No. 5,892,069; U.S. Pat. No. 5,661,143; U.S. Pat. No. 5,504,074; WO 95/04535). Such antiangiogenic activity is likely due to the arrest of endothelial cell mitosis and the consequent prevention of endothelial cell proliferation. 2-alkoxy estradiols exhibiting antiangiogenic activity may be used to treat diseases in which angiogenesis plays an important role. Inducing mitotic arrest and preventing angiogenesis will cause tumors to shrink, and the combination of these methods will provide significant advantages over current anticancer therapies. 2-alkoxy estradiols in murine models have been shown to be orally active, and to exhibit no appreciable toxicity at therapeutically effective doses (Fotsis et al., *Nature* 368, pp. 237–239 (1994)).

In general, there is a need in the art to identify additional antiproliferative and antimitotic chemical compounds which provide therapeutic advantages over those compounds currently known and used. Additionally, there is a need to improve the method of synthesis of such compounds in order to provide greater efficiency, yield, and purity in their production.

SUMMARY OF THE INVENTION

The present invention is directed to novel 2-alkoxy estradiols and derivatives of 2-alkoxy estradiols having antiproliferative and antiangiogenic activity. The invention is also directed to methods of preparing and using these novel compounds.

One embodiment of the present invention are compounds represented by the following structural formulas:

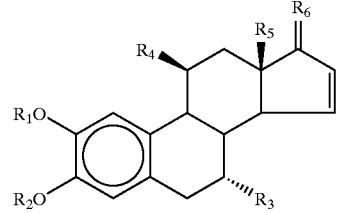

Formula I

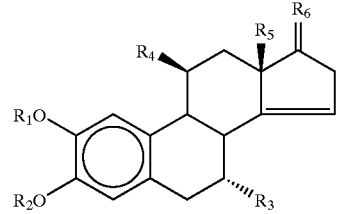

Formula II

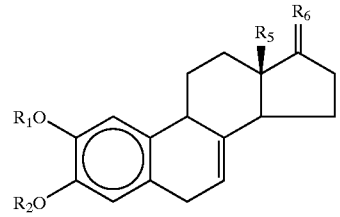

Formula III

-continued

Formula IV

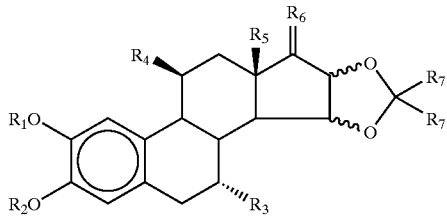

Wherein
R$_1$ is (C$_{1-6}$) alkyl, and optionally substituted by halogen;
R$_2$ is H, or SO$_2$NHR, with R being hydrogen or (C$_{1-6}$) alkyl;
R$_3$ is selected from the group consisting of hydrogen and (C$_{1-6}$) alkyl, and optionally substituted by halogen;
R$_4$ is hydrogen, (C$_{1-6}$) alkyl, (C$_{2-6}$) alkenyl, (C$_{2-6}$) alkynyl, aryl or heteroaryl;
R$_5$ is (C$_{1-2}$) alkyl;
R$_6$ is O, NOR, (H, OR), or (H, OSO$_2$NHR), wherein R is hydrogen, (C$_{1-6}$) alkyl or (C$_{1-6}$) acyl.
R$_7$ is hydrogen or (C$_{1-6}$) alkyl;

The invention includes pharmaceutically acceptable salts or esters, prodrugs and precursors thereof, in admixture with one or more pharmaceutically acceptable carriers, diluents, or excipients therefor.

The term (C$_{1-6}$) alkyl means a branched or unbranched alkyl group having 1–6 carbon atoms. Likewise the term (C$_{1-2}$) alkyl means methyl or ethyl.

The term (C$_{2-6}$) alkenyl means a branched or unbranched alkenyl group having at least one double bond and 2–6 carbon atoms.

The term (C$_{2-6}$) alkynyl means a branched or unbranched alkynyl group having at least one triple bond and 2–6 carbon atoms.

The term aryl means a phenyl group, either unsubstituted or monosubstituted, with groups chosen from (C$_{1-6}$) alkyl, (C$_{2-6}$) alkenyl, (C$_{2-6}$) alkynyl, OR, NHR or NR$_2$, with R being hydrogen or (C$_{1-6}$) alkyl. Preferred aryl groups are substituted in the para position.

The term heteroaryl means a heterocyclic aromatic group such as furanyl, pyrroyl, pyridinyl or thiofuranyl either unsubstituted or monosubstituted, with groups chosen from (C$_{1-6}$) alkyl, (C$_{2-6}$) alkenyl, (C$_{2-6}$) alkynyl, OR, NHR or NR$_2$, with R being hydrogen or (C$_{1-6}$) alkyl.

The term (C$_{1-6}$) acyl means an acyl group derived from a carboxylic acid having 1–6 carbon atoms.

The term halogen means fluorine, chlorine, bromine, or iodine.

Unless noted otherwise, the steroids of this invention have the natural configuration at chiral carbons, that is 8β, 9α, 13β, and 14α. The steroids of this invention may possess also one or more additional chiral carbon atoms. The compounds may therefore be obtained as a pure diasteriomer, or as a mixture of diasteriomers. Methods for obtaining the pure diasteriomers are well known in the art, e.g. crystallization or chromatography.

It is believed by the inventors that by incorporating a double bond in a strategic location in the molecule, such as for example the placement of the double bonds in Formulas I–III above, the conformational change thereby imparted to the molecule may play a significant role in the activity exhibited by the resulting compounds.

Another embodiment of the present invention are novel methods of preparing 2-Methoxyestradiol and 2-Alkoxyestradiol.

Another embodiment of the present invention is a method of making a medicament which is capable of inhibiting undesired cell proliferation, said medicament comprising, in a pharmaceutically acceptable carrier, a cell proliferation inhibiting compound as represented by Formula I, II, III or IV.

Another embodiment of the present invention is a method of treating an individual with cancer. The method comprises administering to the individual a therapeutically effective amount of a compound as represented by Formula I, II, III or IV, or a pharmaceutically acceptable salt thereof. Such treatment may be applied alone or in combination with other therapeutic modalities (e.g., surgery or radiation therapy).

Another embodiment of the present invention is a method of treating an individual with disease(s) characterized by undesirable cell proliferation. The method comprises administering to the individual a therapeutically effective amount of a compound as represented by Formula I, II, III or IV, or a pharmaceutically acceptable salt thereof.

Another embodiment of the present invention is a method of inhibiting cell proliferation. The method comprises contacting the cell, tissue or organ in which cell proliferation is not desired with an effective amount of a compound as represented by Formula I, II, III or IV, or a pharmaceutically acceptable salt thereof.

Another embodiment of the present invention is a method of treating an individual with disease(s) characterized by undesirable angiogenesis. The method comprises administering to the individual a therapeutically effective amount of a compound as represented by Formula I, II, III or IV, or a pharmaceutically acceptable salt thereof.

Another embodiment of the present invention is a method of inhibiting angiogenesis. The method comprises contacting the cell, tissue or organ in or from which angiogenesis is not desired with an effective amount of a compound as represented by Formula I, II, III or IV, or a pharmaceutically acceptable salt thereof.

Another embodiment of the present invention is a method of inhibiting microtubule formation and function. The method comprises contacting cells, tissues or organs in which microtubule formation and function is to be inhibited by an effective amount of a compound as represented by Formula I, II, III or IV, or a pharmaceutically acceptable salt thereof.

The disclosed novel compounds have activity against a variety of tumor cell lines, including ovarian and breast carcinoma, and against proliferation of endothelial cells. These compounds and their use may provide advantages over 2-ME2 and other non-endogenous 2-alkoxyestradiols currently known, and have the potential to be new antitumor, anticancer, anti-microtubule and antiangiogenesis drugs. Additionally, the compounds of the present invention can be used in combination therapy with other known chemotherapeutic or antineoplastic agents (e.g., alkylating agents, antimetabolites, antitumor antibiotics (e.g., vinca alkaloids and taxanes), hormones (e.g., tamoxifen), Selective Estrogen Receptor Modulators (SERMs), antibodies (e.g., Herceptin), and platinum coordination complexes, etc.).

BRIEF DESCRIPTION OF THE DRAWING FIGURES

A more complete understanding of the objects and processes of the present invention may be had by reference to the following detailed description taken in conjunction with the accompanying drawings, wherein.

Figure 4:
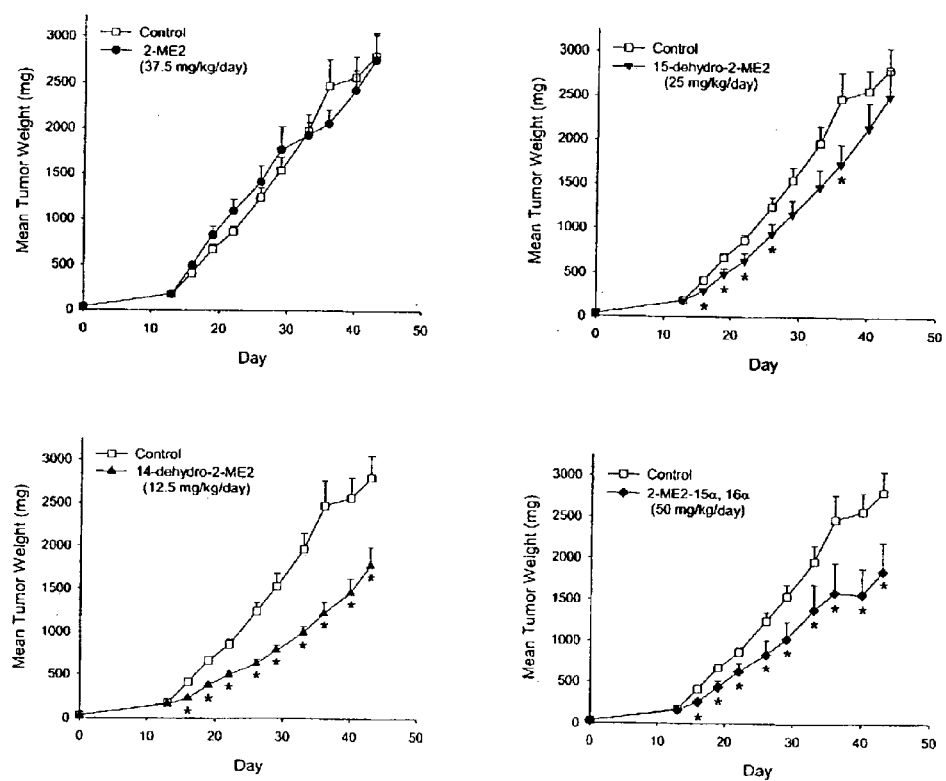
Figure 5:
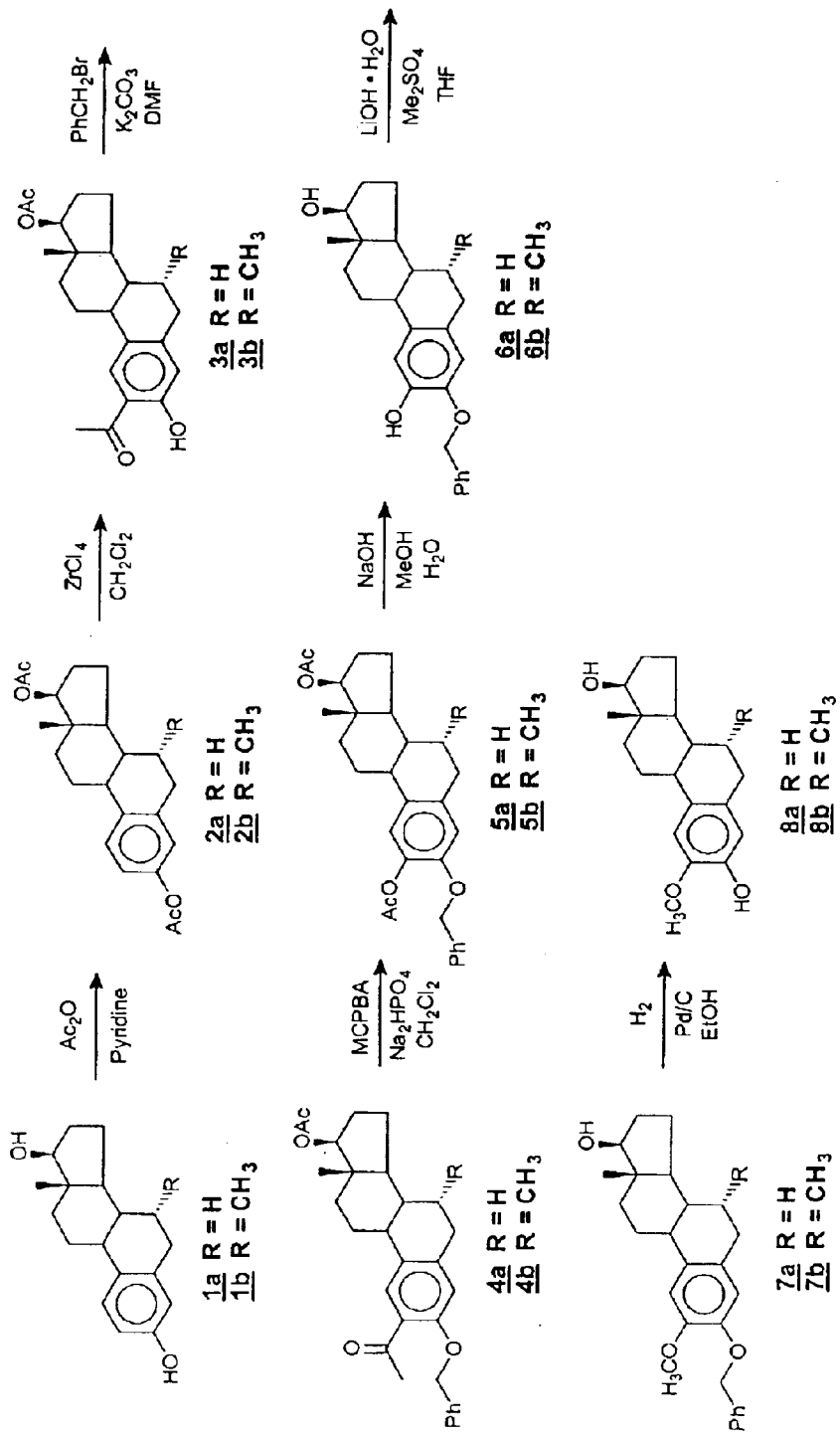
Figure 6:
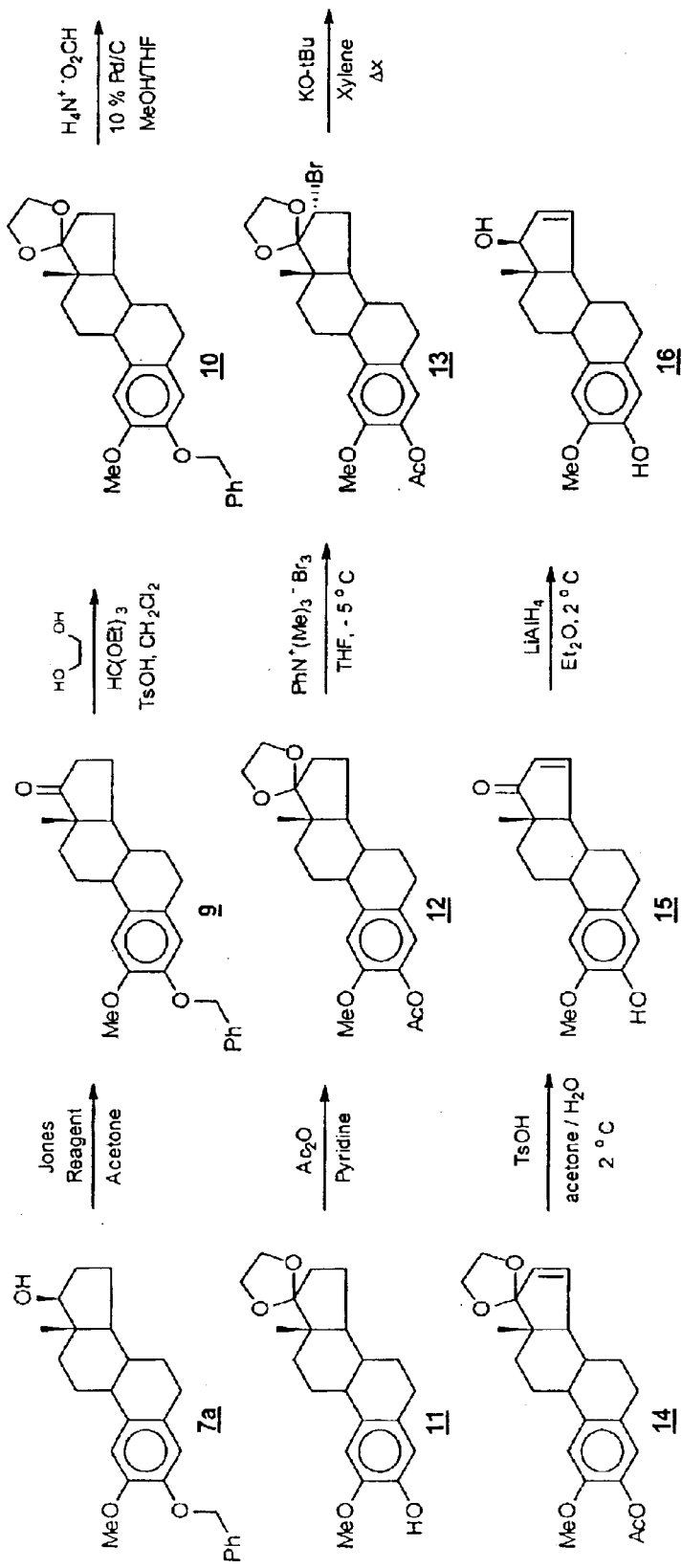
Figure 7:
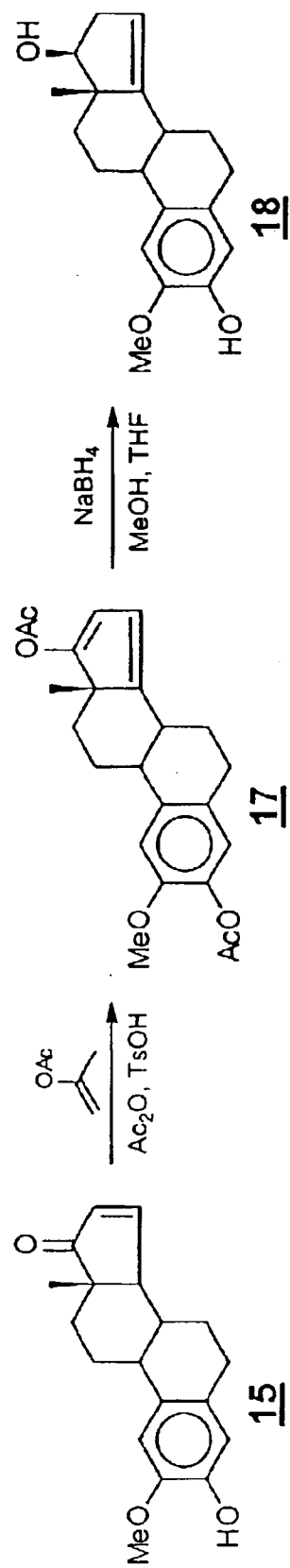
Figure 8:
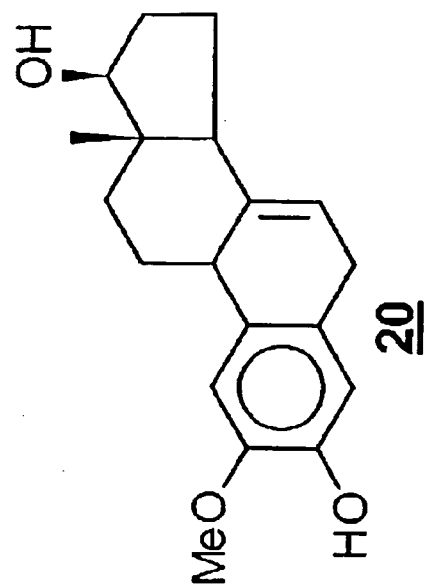
Figure 8:
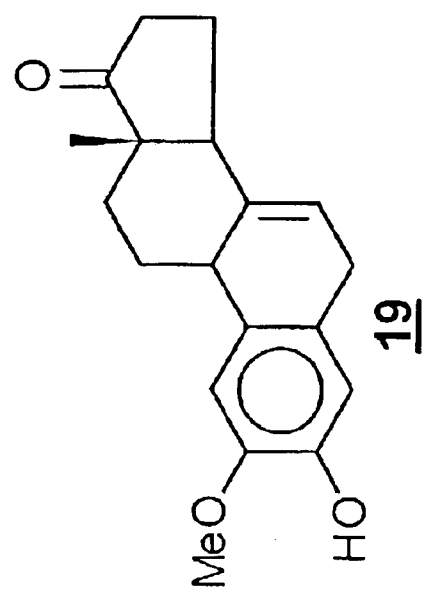
Figure 9:
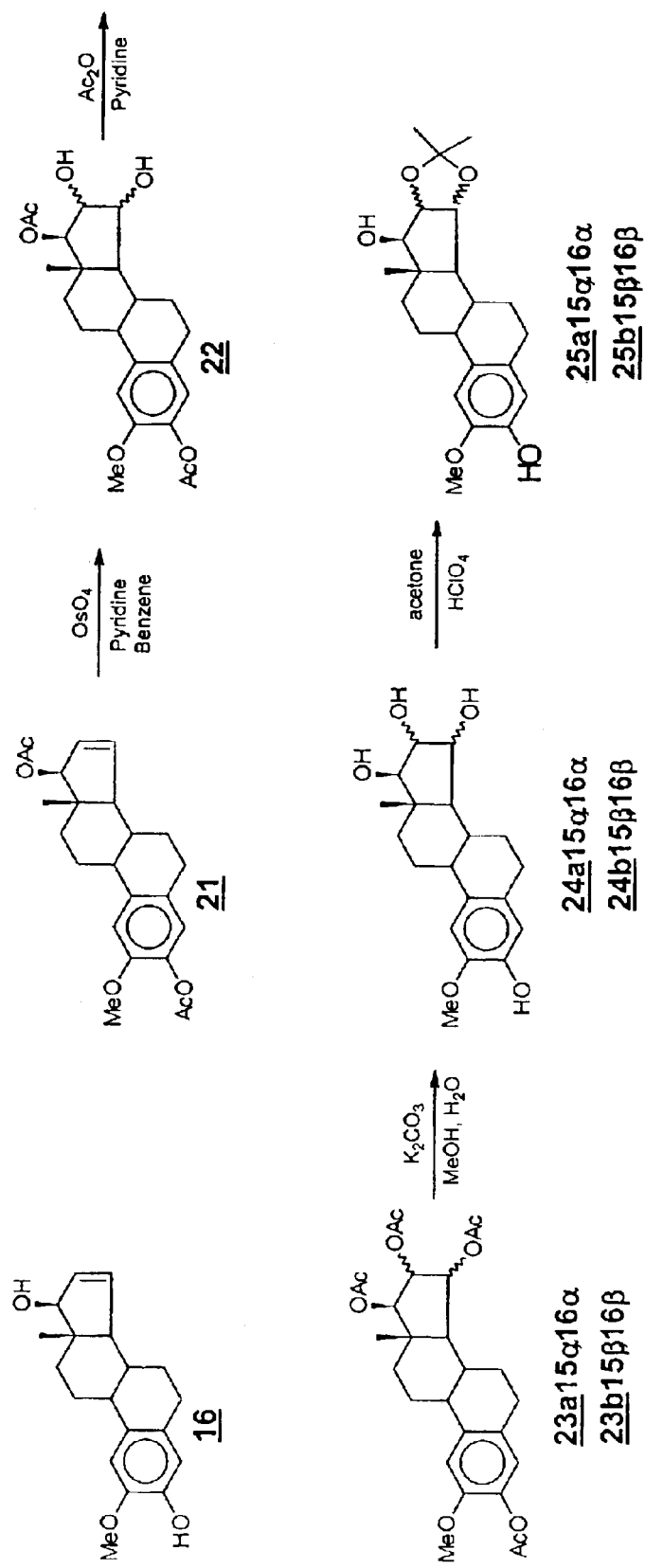

FIG. 4 illustrates the effects of compounds in an MDA-MB-435 breast cancer xenograft model. The data are the means of the groups ±SEM. Statistical significance (P<0.05) is indicated by an asterisk;

FIG. 5 is a schematic showing the synthesis of 2-Methoxyestradiol (8a) and 2-Methoxy-7α-methylestradiol (8b) from estradiol (1a) and 7α-methylestradiol (1b), respectively;

FIG. 6 is a schematic showing the synthesis of 2-Methoxyestra-1,3,5(10),15-tetraen-3,17β-diol (15-dehydro-2-ME2) (16) from 2-Methoxyestradiol 3-benzyl ether (7a);

FIG. 7 is a schematic showing the synthesis of 2-Methoxyestra-1,3,5(10),14-tetraen-3,17β-diol (18) from 2-Methoxyestra-1,3,5(10),15-tetraen-3-ol-17-one (15);

FIG. 8 is a schematic showing the synthesis of 2-Methoxyestra-1,3,5(10),7-tetracn-3,17β-diol (20) from 2-methoxy-3-hydroxyestra-1,3,5(10),7-tetraen-17-one (19); and FIG. 9 is a schematic showing the synthesis of 2-Methoxyestra-1,3,5(10)trien-3,15α,16α17β-tetrol 16,17-acetonide (25a) from 2-Methoxyestra-1,3,5(10),15 tetraen-3,17β-diol (16).

DETAILED DESCRIPTION OF THE INVENTION

The features and details of the invention will now be more particularly described below and pointed out in the claims. It will be understood that the particular embodiments of the invention are shown by way of illustration and not as limitations of the invention. The principal features of this invention may be employed in various embodiments without departing from the scope of the invention.

2-Methoxyestradiol, an example of the class of 2-Alkoxy estradiols, and a numbering system for identifying each carbon atom in the estradiol ring system are shown in the following structural formula:

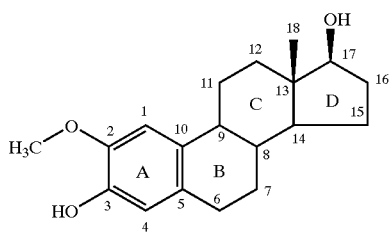

2-Methoxyestradiol (2-ME2)

The novel compounds of the present invention are the compounds represented by the following structural formulas:

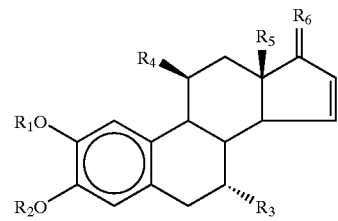

Formula I

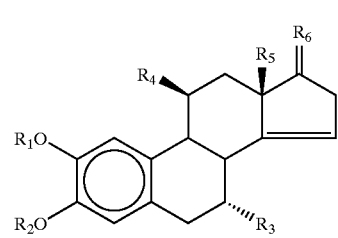

Formula II

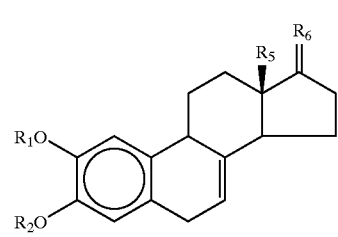

Formula III

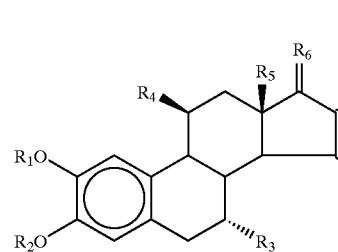

Formula IV

Wherein
$R_1$ is ($C_{1-6}$) alkyl, and optionally substituted by halogen;
$R_2$ is H, or $SO_2NHR$, with R being hydrogen or ($C_{1-6}$) alkyl;
$R_3$ is selected from the group consisting of hydrogen and ($C_{1-6}$) alkyl, and optionally substituted by halogen;
$R_4$ is hydrogen, ($C_{1-6}$) alkyl, ($C_{2-6}$) alkenyl, ($C_{2-6}$) alkynyl, aryl or heteroaryl;
$R_5$ is ($C_{1-2}$) alkyl;
$R_6$ is O, NOR, (H, OR), or (H, $OSO_2NHR$), wherein R is hydrogen, ($C_{1-6}$) alkyl or ($C_{1-6}$) acyl.
$R_7$ is hydrogen or ($C_{1-6}$) alkyl;

The invention includes pharmaceutically acceptable salts or esters, prodrugs and precursors thereof, in admixture with one or more pharmaceutically acceptable carriers, diluents, or excipients therefor.

The term ($C_{1-6}$) alkyl means a branched or unbranched alkyl group having 1–6 carbon atoms. Likewise the term ($C_{1-2}$) alkyl means methyl or ethyl.

The term ($C_{2-6}$) alkenyl means a branched or unbranched alkenyl group having at least one double bond and 2–6 carbon atoms.

The term ($C_{2-6}$) alkynyl means a branched or unbranched alkynyl group having at least one triple bond and 2–6 carbon atoms.

The term aryl means a phenyl group, either substituted or unsubstituted, with groups chosen from $(C_{1-6})$ alkyl, $(C_{2-6})$ alkenyl, $(C_{2-6})$ alkynyl, OR, NHR or $NR_2$, with R being hydrogen or $(C_{1-6})$ alkyl. Preferred aryl groups are substituted in the para position.

The term heteroaryl means a heterocyclic aromatic group such as furanyl, pyrroyl, pyridinyl or thiofuranyl either substituted or unsubstituted, with groups chosen from $(C_{1-6})$ alkyl, $(C_{2-6})$ alkenyl, $(C_{2-6})$ alkynyl, OR, NHR or $NR_2$, with R being hydrogen or $(C_{1-6})$ alkyl.

The term $(C_{1-6})$ acyl means an acyl group derived from a carboxylic acid having 1–6 carbon atoms.

The term halogen means fluorine, chlorine, bromine, or iodine.

Unless noted otherwise, the steroids of this invention have the natural configuration at chiral carbons, that is $8\beta$, $9\alpha$, $13\beta$, and $14\alpha$. The steroids of this invention may possess also one or more additional chiral carbon atoms. The compounds may therefore be obtained as a pure diasteriomer, or as a mixture of diasteriomers. Methods for obtaining the pure diasteriomers are well known in the art, e.g. crystallization or chromatography.

It is believed by the inventors that by incorporating a double bond in a strategic location in the molecule, such as for example the placement of the double bonds in Formulas I–III above, the conformational change thereby imparted to the molecule may play a significant role in the activity exhibited by the resulting compounds.

Table 1 below sets forth the novel chemical structures of the species of the compounds represented by Formulas I, II, III and IV, respectively, which the inventors have discovered, synthesized and tested for the purposes of the present invention. Table 1 also sets forth the full names of the chemical structures tested alongside the abbreviations by which these structures will be referenced herein below for purposes of simplification. It will be apparent to those skilled in the art that the compositions set forth in Table 1 may be modified and derivatives created, also by methods known to those skilled in the art, to include the additional and alternative chemical side groups appearing in Formulas I, II, III and IV without affecting chemical activity, as set forth herein (*The Merck Index*, 11th Ed., Merck & Co., Inc., Rahway, N.J. USA, pp. 583–584 (1989)). It will also be appreciated by those skilled in the art that a wide range of equivalents exist to the chemical side groups appearing in Formulas I, II, III and IV. Such equivalents are intended to be within the scope and spirit of the present invention.

TABLE 1

Chemical structures, names and abbreviations

| COMPOUND | NAME | ABBREVIATION |
|---|---|---|
| (structure) | 2-Methoxyestradiol | 2-ME2 |
| (structure) | 2-Methoxyestra-1,3,5(10), 15-tetraen-3,17β-diol | 15-dehydro-2-ME2 |
| (structure) | 2-Methoxyestra-1,3,5(10), 14-tetraen-3,17β-diol | 14-dehydro-2-ME2 |
| (structure) | 2-Methoxyestra-1,3,5(10), 7-tetraen-3,17β-diol | 7-dehydro-2-ME2 |

TABLE 1-continued

Chemical structures, names and abbreviations

| COMPOUND | NAME | ABBREVIATION |
|---|---|---|
| (structure) | 2-Methoxy-3,15α,16α,17β-tetrahydroxyestra-1,3,5(10)-triene 15,16-acetonide | 2-ME2-15α,16α |

As will be appreciated from the examples below, the compounds of the present invention, represented by Formulas I, II, III and IV, inhibit cell growth, exhibit anti-mitotic properties, inhibit microtubule formation and function, and inhibit angiogenesis including the proliferation and invasion of endothelial cells. As a result of their properties, the compositions of the present invention may be used, among other things, to inhibit tumor cell growth, inhibit undesired cell proliferation and to inhibit angiogenesis.

Indications

The compounds of the invention may be used to treat any disease characterized by abnormal or undesired cell proliferation. Such diseases include for example, but are not limited to: abnormal stimulation of endothelial cells (e.g., atherosclerosis), solid tumors and tumor metastasis, benign tumors (e.g., hemangiomas, acoustic neuromas, neurofibromas, trachomas and pyogenic granulomas), vascular malfunctions, abnormal wound healing, inflammatory and immune disorders, Bechet's disease, gout or gouty arthritis, abnormal angiogenesis accompanying for example rheumatoid arthritis, psoriasis, diabetic retinopathy, and other ocular angiogenic diseases such as retinopathy of prematurity (retrolental fibroplasia), macular degeneration, corneal graft rejection, neuroscular glaucoma and Oster Webber syndrome.

Neoplasms which the compounds of the invention may be used to treat include: mammary, small-cell lung, non-small-cell lung, colorectal, leukemia, lymphoma, melanoma, pancreatic, renal, liver, mycloma, multiple mycloma, mesothelioma, central nervous system including neuroblastoma, ovarian, prostate, sarcoma of soft tissue or bone, head and neck, esophageal, stomach, bladder, retinoblastoma, squamous cell, testicular, vaginal, and neuroendocrine-related which includes thyroid, Hodgkin's disease and non-Hodgkin's disease neoplasms.

In another embodiment of the invention, the compounds of the present invention can be used in combination with other treatment modalities, e.g. surgery or radiation therapy, and in combination therapy with other known chemotherapeutic or antineoplastic agents (e.g., alkylating agents, antimetabolites, antitumor antibiotics, antimitotics (e.g., vinca alkaloids and taxanes), hormones (e.g., tamoxifen), Selective Estrogen Receptor Modulators (SERMs), antibodies (e.g., Herceptin), and platinum coordination complexes, etc.). For example, the compounds of the present invention can be used in combination therapy with a vinca alkaloid compound, such as vinblastine, vincristine, Taxol®, etc.; an antibiotic, such as adriamycin (doxorubicin), dactinomycin (actinomycin D), daunorubicin (daunomycin, rubidomycin), bleomycin, plicamycin (mithramycin) and mitomycin (mitomycin C), etc.; an antimetabolite, such as methotrexate, cytarabine, azauridine, azaribine, fluorodeoxyuridine, deoxycoformycin, mercaptopurine, etc.; or a platinum coordination complex, such as cisplatin, carboplatin, etc. In addition, those of skill in the art will appreciate that the compounds of the present invention can be used in combination therapy with other known chemotherapeutic or antineoplastic compounds.

In another embodiment this invention relates to a method of treating diseases associated with undesired angiogenesis, the method comprising administering to an individual an anti-angiogenic compound of Formula I, II, III or IV, or a pharmaceutically acceptable salt or ester thereof, prodrug or precursor thereof, in admixture with one or more pharmaceutically acceptable carriers, diluents, or excipients therefor, in a therapeutically effective amount.

The methods of the present invention may be used to treat a variety of diseases. Diseases associated with corneal neovascularization that can be treated according to the present invention include, but are not limited to, diabetic retinopathy, retinopathy of prematurity, corneal graft rejection, neovascular glaucoma and retrolental fibroplasias, epidemic keratoconjunctivitis, Vitamin A deficiency, contact lens overwear, atopic keratitis, superior limbic keratitis, pterygium keratitis sicca, sjogrens, acne rosacea, phylectenulosis, syphilis, mycobacterial infections, lipid degeneration, chemical burns, bacterial ulcers, fungal ulcers, Herpes simplex infections, Herpes zoster infections, protozoan infections, Kaposi's sarcoma, Mooren ulcer, Terrien's marginal degeneration, marginal keratolysis, trauma, rheumatoid arthritis, systemic lupus, polyarteritis, Wegeners sarcoidosis, scleritis, Steven Johnson's disease and periphigoid radial keratotomy.

Diseases associated with retinal/choroidal neovascularization that can be treated according to the present invention include, but are not limited to, diabetic retinopathy, macular degeneration, sickle cell anemia, sarcoid, syphilis, pseudoxanthoma elasticum, Pagets disease, vein occlusion, artery occlusion, carotid obstructive disease, chronic uveitis/vitritis, mycobacterial infections, Lyme's disease, systemic lupus erythematosus, retinopathy of prematurity, Eales disease, Bechets disease, infections causing a retinitis or choroiditis, presumed ocular histoplasmosis, Bests disease, myopia, optic pits, Stargarts disease, pars planitis, chronic retinal detachment, hyperviscosity syndromes, toxoplasmosis, trauma and post-laser complications. Other diseases include, but are not limited to, diseases associated with rubeosis (neovascularization of the angle) and diseases caused by the abnormal proliferation of fibrovascular or fibrous tissue, including all forms of proliferative vitreoretinopathy, whether or not associated with diabetes.

Diseases associated with chronic inflammation can also be treated using the methods of the present invention.

Diseases with symptoms of chronic inflammation include, but are not limited to, inflammatory bowel diseases, such as Crohn's disease and ulcerative colitis, psoriasis, sarcoidosis and rheumatoid arthritis. Unwanted angiogenesis is a key element that these chronic inflammatory diseases have in common. The chronic inflammation depends on continuous formation of capillary sprouts to maintain an influx of inflammatory cells.

Other diseases that can be treated using the methods and compositions of the present invention include endometriosis, hemangiomas, Osler-Weber-Rendu disease, or hereditary hemorrhagic telagiectasia, solid or blood borne tumors and acquired immune deficiency syndrome (AIDS).

The compositions and methods of the present invention can also be used to treat diseases, other than cancer for example, in which normal tubulin polymerization and function plays a role. Chagas' disease, for example, is caused by *Trypanosoma cruzi*, a flagellate protozoa which has a substantial protein composition containing tubulin both as a component of the subpellicular microtubule system and the flagellum. Chagas' disease is characterized by lesions in the heart, alimentary tract and nervous system. The disease is the leading cause of myocarditis in the Americas. Inhibition of tubulin polymerization, crucial to the parasite's mobility, would provide an effective treatment. Indeed, the use of agents that selectively affect tubulin polymerization has precedence in the therapy of other parasitic diseases. The benzimidazoles are very effective anti-helmenthic drugs, and the dinitroanilines have shown promise against *Leishmania*, a parasite closely related to *Trypanosoma* (U.S. Pat. No. 6,162,930). The compositions of the present invention may be used to contact such parasites or sites of parasitic infection and thereby treat the associated disease.

Another embodiment of this invention relates to a method of treating fungal diseases, the method comprising administering a therapeutically effective amount of a compound of Formula I, II, III or IV, or a pharmaceutically acceptable salt or ester, prodrug or precursor thereof, in admixture with one or more pharmaceutically acceptable carriers, diluents, or excipients therefor. The progression of fungal diseases has proven particularly susceptible to treatment by drugs that act by disruption of microtubule organization, as for example by cryptophycin (U.S. Pat. No. 6,180,679). The methods of the present invention may be used in controlling mycotic infections or in controlling a yeast infection, where controlling refers to slowing, stopping or interrupting the spread of the given infection and not necessarily to a complete and total elimination of the mycotic infection or yeast infection.

Administration

The compositions described above may be provided in therapeutically effective amounts as physiologically acceptable formulations using known techniques, and these formulations may be administered by standard routes. In general, the compositions may be administered alone or in combination, and by topical, oral, rectal, intravenous, subcutaneous or intramuscular route. In addition, the compounds may be incorporated into biodegradable polymers allowing for sustained release, the polymers being implanted in the vicinity of where delivery is desired, for example, at the site of a tumor. Biodegradable polymers and their use are described in detail in Brem et al., *J. Neurosurg.* 74, 441–446 (1991), and are familiar to those skilled in the art.

As will be appreciated by one skilled in the art, the dosage of the composition will depend on the condition being treated, the particular compound used, the type and severity of the disease or malady, and other clinical factors such as weight, sex, age and condition of the patient, the patient's tolerance to drugs and/or treatment, and the route of administration. Those skilled in the art will be able to determine the appropriate dosages depending on these and other factors. Typically, a therapeutically effective amount of the compound can range from about 1 mg per day to about 1000 mg per day for an adult human individual. For oral administration to human adults, a dosage of 0.01 to 100 mg/kg/day, preferably 0.01–1 mg/kg/day, is generally a therapeutically effective amount.

The formulations include those suitable for oral, rectal, nasal, topical (including buccal and sublingual), vaginal or parenteral (including subcutaneous, intramuscular, intravenous, intradermal, intraocular, intratracheal and epidural) administration. The formulations may conveniently be presented in unit dosage form and may be prepared by conventional pharmaceutical techniques. Such techniques may include the step of bringing into association the active ingredient and the pharmaceutical carrier(s) or excipient(s). Pharmaceutical carriers or excipients may contain inert ingredients which do not interact with the compound, or ingredients that do interact with the compound but not in a fashion so as to interfere with the desired effect. In general, the formulations are prepared by uniformly and intimately bringing into association the active ingredient with liquid carriers or finely divided solid carriers or both, and then, if necessary, shaping the product.

Formulations of the present invention suitable for oral administration may be presented as discrete units such as capsules, cachets or tablets each containing a predetermined amount of the active ingredient; as a powder or granules; as a solution or a suspension in an aqueous liquid or non-aqueous liquid; or as an oil-in-water liquid emulsion or a water-in-oil emulsion and as a bolus, et cetera.

A tablet may be made by compression or molding, optionally with one or more accessory ingredients. Compressed tablets may be prepared by compressing, in a suitable machine, the active ingredient in a free-flowing form such as a powder or granules, optionally mixed with a binder, lubricant, inert diluent, preservative, surface-active or dispersing agent. Molded tablets may optionally be coated or scored and may be formulated so as to provide a slow or controlled release of the active ingredient therein.

Formulations suitable for topical administration in the mouth include lozenges comprising the ingredients in a flavored basis, usually sucrose and gum acacia or gum tragacanth; pastilles comprising the active ingredient in an inert basis such as gelatin and glycerin, or sucrose and gum acacia; and mouthwashes comprising the ingredient to be administered in a suitable liquid carrier.

Formulations suitable for topical administration to the skin may be presented as ointments, creams, gels and pastes comprising the ingredient to be administered in a pharmaceutically acceptable canrier. A preferred topical delivery system is a transdermal patch containing the ingredient to be administered.

Formulations for rectal administration may be presented as a suppository with a suitable base comprising, for example, cocoa butter or a salicylate.

Formulations suitable for nasal administration, wherein the carrier is a solid, include a coarse powder having a particle size, for example, in the range of 20 to 500 microns which is administered by rapid inhalation through the nasal passage from a container of the powder held close to the nose. Suitable formulations for administration wherein the carrier is a liquid, for example, are nasal sprays or nasal drops including aqueous or oily solutions of the active ingredient.

Formulations suitable for vaginal administration may be presented as pessaries, tampons, creams, gels, pastes, foams or spray formulations containing in addition to the active ingredient such carriers as are known by those skilled in the art to be appropriate.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze-dried (lyophilized) condition requiring only the addition of the sterile liquid carrier, for example, water for injection, immediately prior to use. Extemporaneous injection solutions and suspensions may be prepared from sterile powders, granules and tablets of the kind previously described herein.

In addition, the compositions of the present invention may be administered in a formulation including liposomes in order to improve availability and to regulate dosage. The liposome may or may not form part of a targeted drug delivery system, for example in a liposome coated with a tumor-specific antibody. Such liposomes will be targeted to and taken up selectively by the site of interest (e.g., a tumor cell) Liposomes and emulsions are well known examples of delivery vehicles or carriers. Further, long-circulating, or stealth, liposomes may be employed (U.S. Pat. No. 5,013, 556) (incorporated herein by reference).

Generally, such liposomes or other drug delivery systems typically have a targeting moiety, i.e., ligand, conjugated thereto that is specific for the target site of interest (e.g., tumor cell). For instance, some property (biochemical, architectural or genetic) of the tumor that is different from normal tissue can be exploited to concentrate the compounds of the present invention in, or at least near, the target tumor. Tumor vasculature, which is composed primarily of endothelial cells, is inherently different than normal differentiated vasculature. For example, the architecture of tumor vasculature is known to be leaky, and blood flow through them is mostly intermittent, with periods of perfusion and periods of occlusion and subsequent hypoxia. This aberrant microenvironment may be caused by and, in turn, leads to, additional differential gene expression in tumor vasculature relative to normal vasculature. This abnormal architecture and function, at the molecular level, is characterized by differences in surface markers in tumor microvessels relative to normal vessels and such differences can be exploited to target the liposome or other drug delivery system to the site of interest. Liposomes offer the added advantage of shielding the drug from most normal tissues. When coated with polyethylene glycol (PEG) (i.e., stealth liposomes) to minimize uptake by phagocytes and with a tumor vasculature-specific targeting moiety, liposomes offer longer plasma half-lives, lower non-target tissue toxicity and delivery, and increased efficacy over non-targeted drug.

Other targeting strategies include, but are not limited to, ADEPT (antibody-directed enzyme prodrug therapy), GDEPT (gene-directed EPT) and VDEPT (virus-directed EPT). In ADEPT, the targeting of an inactive prodrug to a tumor mass is effected by an antibody against a tumor-associated marker. The enzyme milieu in or about the tumor transforms the prodrug into an active toxic agent that then acts on the tumor tissue. Similarly, differential gene expression or viral targeting at the tumor site is used to activate a prodrug into its active, toxic form in GDEPT and VDEPT, respectively. Other strategies include targeting differentially expressed genes, enzymes or surface markers that appear on, for example, tumor-associated vasculature to effect control of tumor progression or to other sites of interest (e.g., endothelial cells, TNF-α, TNF-α receptor, etc.).

Additionally, standard pharmaceutical formulation techniques may be employed such as those described in Remington's Pharmaceutical Sciences, Mack Publishing Company, Easton, Pa. Additional methods of encapsulating compounds or compositions comprising the compound are known to those skilled in the art (Baker et al., "Controlled Release of Biological Active Agents", John Wiley and Sons, 1986).

Preferred unit dosage formulations are those containing a daily dose or unit, daily sub-dose, as herein above recited, or an appropriate fraction thereof, of the administered ingredient.

It should be understood that in addition to the ingredients specifically set forth above, the formulations of this invention may include other agents conventional in the art having regard to the type of formulation in question, for example, those suitable for oral administration may include flavoring and other agents.

Definitions

"Angiogenesis" refers to the generation or creation of new blood vessels into tissue, organs or tumors.

An "individual" is preferably a human, but can also be animals in need of treatment, e.g., veterinary animals (such as dogs, cats and the like), farm animals (such as cows, pigs, horses and the like) and laboratory animals (such as rats, mice, guinea pigs and the like).

A "therapeutically effective amount" is the quantity of compound which results in an improved clinical outcome as a result of the treatment compared with a typical clinical outcome in the absence of the treatment. An "improved clinical outcome" includes a longer life expectancy or relief of unwanted symptoms for the individual receiving treatment. It can also include slowing or arresting the rate of growth of a tumor, causing shrinkage in the size of the tumor, a decreased rate of metastasis, and/or a decreased rate of abnormal or undesired proliferation and/or angiogenesis. It can also include inhibition of microtubule formation and function, and inhibition of normal tubulin function.

An "effective amount" or "amount sufficient" refers to an amount of compound or composition effective to depress, suppress or regress the undesired activity.

"Pharmaceutically acceptable salt" refers to those salts of compounds which retain the biological effectiveness and properties of the compounds and which are obtained by reaction with inorganic acids such as hydrochloric acid, hydrobromic acid, sulfuric acid, nitric acid, or phosphoric acid; or by reaction with organic acids such as methanesulfonic acid, ethanesulfonic acid, p-toluenesulfonic acid, salicylic acid and the like. Pharmaceutically acceptable salts include, for example, alkali metal salts, such as sodium and potassium, alkaline earth salts and ammonium salts; esters; prodrugs and precursors thereof, in admixture with one or more pharmaceutically acceptable carriers, diluents, or excipients therefor.

"Contacting" is used herein interchangeably with the following: combined with, added to, mixed with, passed over, incubated with, rowed over, etc.

"Inhibit" is defined to include its generally accepted meaning which includes prophylactically treating a cell, tissue, organ or individual, treating a cell, tissue, organ or individual, and/or holding in check and/or treating existing conditions, and includes medical, clinical, therapeutic and/or prophylactic use of the compounds of the invention.

EXAMPLE 1

Properties of the Compounds

Four novel derivatives of 2-ME2 were designed, synthesized and tested for antiproliferative activity against breast, prostate, cervical and ovarian cancer cells. These analogs are shown above in Table 1. As set forth in more detail below, one analog is 3-to 25 times more potent than 2-ME2 and another is approximately equal in potency, while two others were slightly less potent against 6 human tumor cell lines. All 4 analogs disrupt interphase and mitotic microtubules, consistent with the current state of knowledge of the mechanism of action of 2-ME2.

The antiangiogenic activity of 2-ME2 is of key importance in its antitumor effects. The effects of the 4 analogs on the proliferation of endothelial cells, an indicator of antiangiogenic activity, were evaluated. All 4 analogs inhibited endothelial cell proliferation. These data are consistent with the known effects of antiangiogenic compounds.

The 2-ME2 analogs were also tested for effectiveness against a multi-drug resistant cell line (NCI/ADR). This cell line is over 2000-fold resistant to Taxol®, a highly successful anticancer agent. The new analogs were highly effective against the multi-drug resistant cell line which is known to overexpress the drug-efflux pump P-glycoprotein, suggesting that they are not substrates for transport by P-glycoprotein. The overexpression of such drug efflux pumps in human tumors leads to multi-drug resistance and failure of chemotherapy. The ability to circumvent drug resistance mechanisms provides a significant advantage for potential chemotherapeutic agents.

The 4 analogs of 2-ME2 set forth in Table 1 were tested for antiproliferative activity against 6 human tumor cell lines. The SK-OV-3 cell line was derived from ovarian carcinoma, the MDA-MB-435 and NCI/ADR from breast adenocarcinoma, PC3 and DU 145 from prostate carcinoma and HeLa from cervical carcinoma. The SK-OV-3, HeLa, PC3, and DU 145 and cell lines were obtained from the American Type Culture Collection, 10801 University Blvd., Manassas, Va. 20110-2209. The MDA-MB-435 cell line was obtained from the Lombardi Cancer Center of Georgetown University School of Medicine and the NCI/ADR cell line was obtained from the National Cancer Institute, Fairview Center, Suite 204, 1003 West 7th Street, Frederick, Md. 21701-8531.

Cells were plated into 96 well plates and allowed to grow and attach for 18–24 hours and then the drugs or vehicle controls were added to the wells. Each data point represents the mean of three experiments, each of which consisted of three replicates within an experiment. The cells were incubated with the drugs for 48 hours and then the cellular protein was fixed and quantified using the sulforhodamine B (SRB) assay. The absorbance of the dye is linear with respect to both cell protein and cell number (Skehan, P.; Storeng, R.; Scudiero, D., Monks; A., McMahon, J.; Vistica, D., Warren, J. T.; Bokesch, H., Kenney, S.; and Boyd, M. R., "New colorimetric cytotoxicity assay for anticancer-drug screening", *J. Natl. Cancer Inst*, 82, 1107–1112 (1990)). The effects of the drugs were compared to vehicle controls and the data plotted as percent of control vs. log of drug concentration.

Figure 1:
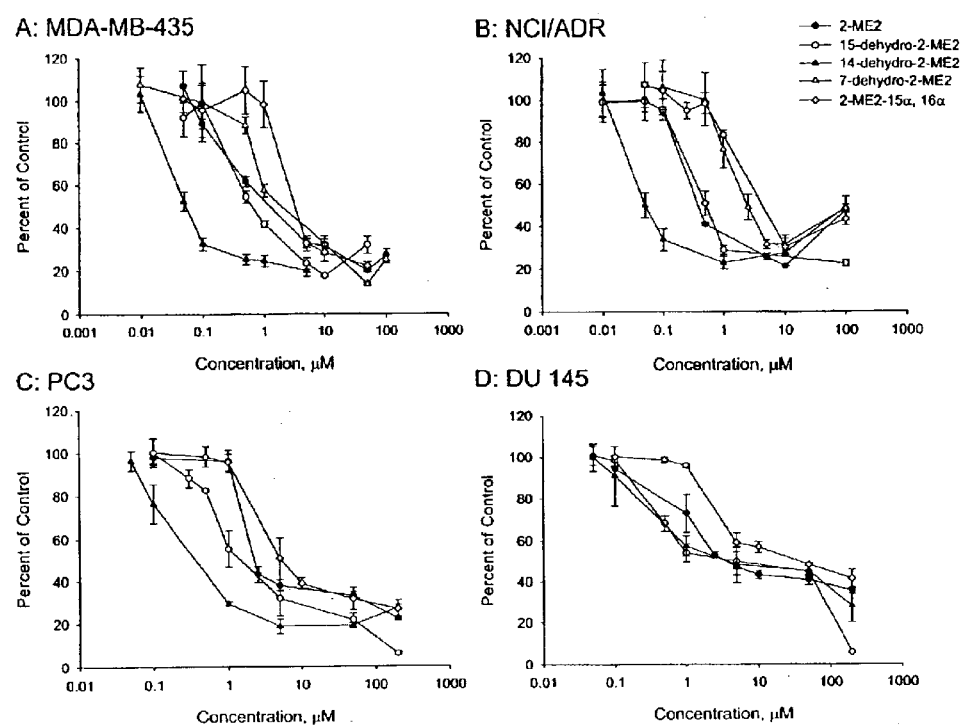
FIG. 1 illustrates the dose response curves for inhibition of cancer cell proliferation of four cell lines by 2-ME2 and each of the four compositions of the invention. The sulforhodamine B (SRB) assay, referenced in Example 1, was used to construct dose response curves in MDA-MB-435 (A), NCI/ADR (B), PC3 (C), and DU 145 cells(D), n=3±SD.

The dose response curves for 2-ME2 and the 4 analogs in 4 human tumor cell lines are presented in FIG. 1. The $IC_{50}$ is defined as the drug concentration required to inhibit cell proliferation 50% and is calculated from the linear portion of the log concentration response curve. The $IC_{50}$ value for each of the analogs was determined in the 6 human tumor cell lines and the data are presented in Table 2:

TABLE 2

The $IC_{50}$ values for inhibition of proliferation of drug sensitive and a multidrug resistant cancer cell lines.

| | $IC_{50}$ (μM) | | | | |
|---|---|---|---|---|---|
| | 2-ME2 | 15-dehydro-2-ME2 | 14-dehydro-2-ME2 | 7-dehydro-2-ME2 | 2-ME2-15α, 16α |
| MDA-MB-435 | 1.38 ± 0.10 | 0.86 ± 0.11 | 0.056 ± 0.002 | 1.97 ± 0.40 | 3.24 ± 0.35 |
| NCI/ADR | 0.38 ± 0.01 | 0.49 ± 0.06 | 0.056 ± 0.01 | 2.54 ± 0.44 | 4.21 ± 0.60 |
| PC3 | 2.22 ± 0.15 | 1.82 ± 0.98 | 0.35 ± 0.09 | ND | 5.13 ± 1.53 |
| DU 145 | 4.26 ± 0.95 | 1.25 ± 0.32 | 1.58 ± 0.81 | ND | 6.78 ± 0.62 |
| HeLa | 0.45 ± 0.04 | 0.43 ± 0.08 | 0.05 ± 0.02 | ND | 2.98 ± 0.24 |
| SK-OV-3 | 1.79 ± 0.24 | 1.37 ± 0.26 | 0.15 ± 0.07 | 4.49 ± 0.18 | 5.16 ± 0.99 |

The $IC_{50}$ values for inhibition of proliferation were calculated from the log dose response curve (n=3, mean±SD).

15-dehydro-2-ME2 is approximately equal in potency to 2-ME2 against the MDA-MB-435, NCI/ADR, PC3, HeLa and SK-OV-3 cell lines and is over three times more potent towards the DU 145 cell line. In 5 of the 6 cell lines tested, 14-dehydro-2-ME2 is substantially (6–24 fold) more potent than 2-ME2, and it is 2.7 fold more potent in the DU 145 cell line. 7-Dehydro-2-ME2 and 2-ME2-15α,16α are generally less potent than 2-ME2, yet 7-dehydro-2-ME2 is almost equipotent against the MDA-MB-435 cell line. The data suggest that there may be different chemosensitivity to these estradiol derivatives.

The effects of the analogs on a multi-drug resistant cell line were also studied. The NCI/ADR cell line is resistant to many chemotherapeutic agents by virtue of its high expression of the drug efflux pump P-glycoprotein. The effects of 2-ME2 and the analogs on the proliferation of NCI/ADR are presented in FIG. 1B. The NCI/ADR cell line was obtained from the National Cancer Institute, Fairview Center, Suite 204, 1003 West 7th Street, Frederick, Md. 21701-8531. As will be noted from FIG. 1B, the estradiol derivatives are active against the drug resistant cell line. The $IC_{50}$ data are presented in Table 3:

TABLE 3

Inhibition of proliferation of a drug sensitive and a multidrug resistant cell line.
IC$_{50}$ Values

|  | 2-ME2 ($\mu$M) | 15-dehydro-2-ME2 ($\mu$M) | 14-dehydro-2-ME2 ($\mu$M) | 7-dehydro-2-ME2 ($\mu$M) | 2-ME2-15$\alpha$, 16$\alpha$ ($\mu$M) | Taxol ® ($\mu$M) | Vinblastine ($\mu$M) |
|---|---|---|---|---|---|---|---|
| NCI-ADR | 0.38 ± 0.01 | 0.49 ± 0.06 | 0.056 ± 0.01 | 2.54 ± 0.44 | 4.21 ± 0.60 | 4.46 ± 0.61 | 0.43 ± 0.07 |
| MDA-MB-435 | 1.38 ± 0.10 | 0.86 ± 0.11 | 0.056 ± 0.002 | 1.97 ± 0.40 | 3.24 ± 0.35 | 0.00201 ± 0.0003 | 0.00308 ± 0.00009 |
| NCI-ADR/ MDA-MB-435 resistance factor | 0.28 | 0.57 | 1.0 | 1.29 | 1.30 | 2218.91 | 139.61 |

The IC$_{50}$ values for inhibition of proliferation were calculated from the dose-response curves. The values represent the mean of 3 experiments ±SD. Resistance factors were calculated by dividing the IC$_{50}$ of the resistant cell line, NCI/ADR, by the IC$_{50}$ in a drug sensitive cell line, MDA-MB-435. The resistance factors for Taxol® and vinblastine are 2,218 and 140 respectively. These values are not surprising because they are known substrates of P-glycoprotein. This data suggests that these estradiol derivatives are not substrates for P-glycoprotein-mediated transport.

Figure 2:
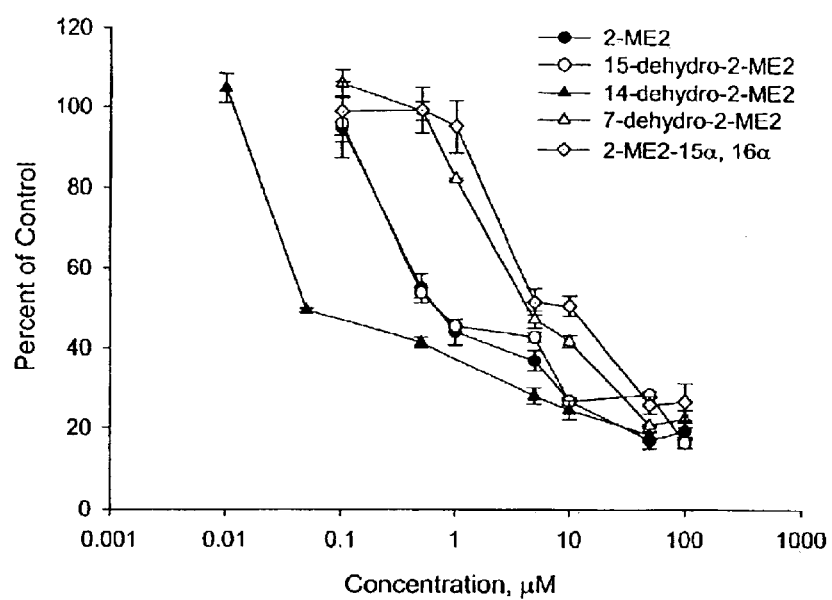
FIG. 2 illustrates the effects of compounds on Human Umbilical Vein Endothelial Cells (HUVEC) proliferation. The SRB assay was used to construct the dose response curves of the agents in HUVEC cells. n=3±SD.
Figure 3:
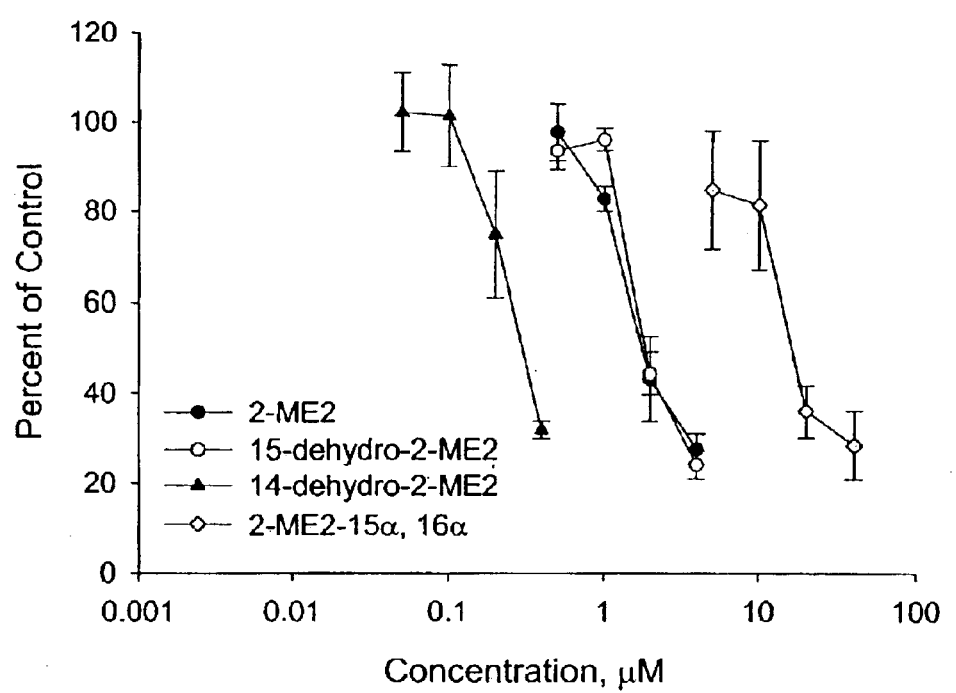
FIG. 3 illustrates the effects of compounds on Human Umbilical Vein Endothelial Cells (HUVEC) cell invasion. Becton-Dickinson (BD) Biocoat® Matrigel® invasion chambers were used to construct dose response curves of the compounds for invasion of HUVECs. n=3±SD.

Two in vitro assays were used to detect the potential for antiangiogenic activity of the analogs. One assay tested the ability of the analogs to inhibit the cellular proliferation of endothelial cells as shown below (Table 4). The ability of the analogs to inhibit the proliferation of endothelial cells was tested and compared to the effects of 2-ME2. Drugs that have antiangiogenic activity inhibit the proliferation of endothelial cells. As demonstrated in FIG. 2, all the analogs were active against endothelial cells with a profile similar to the effects in tumor cells. The IC$_{50}$ values were calculated from the dose-response curves and are presented in Table 4:

HUVECs were obtained from BioWhittaker and were used during passages of 2 to 6. BD Biocoat® Matrigel® invasion chambers were used for the assays. These modified Boyden chambers have a PET membrane with 8 $\mu$m pores that have been coated with Matrigel®. The membrane separates the upper chamber from the lower chamber. HUVECs were plated into the top chamber in media containing 0.1% bovine serum albumin with either a test compound or vehicle and allowed to invade and migrate through pores for 24 hours. The media in the lower chamber contained the chemoattractant, 10% fetal bovine, serum. Following the incubation period the cells on the top of the membrane were removed with a cotton swab and the cells that had migrated through the pores to the lower surface of the membrane were stained with hematoxylin and eosin and counted microscopically. Experiments were conducted in duplicate and the numbers of cells that migrated were counted in 10 microscope fields per transwell chamber. The data are expressed as percent of vehicle control invasion. Dose response curves were generated and are shown in FIG. 3 and the IC$_{50}$s for inhibition of HUVEC invasion were determined and are presented above in Table 4. All of the 2-ME2 analogs

TABLE 4

Inhibitory effects of 2-ME2 and analogs towards HUVEC proliferation and invasion.
IC$_{50}$ ($\mu$M)

|  | 2-ME2 | 15-dehydro-2-ME2 | 14-dehydro-2-ME2 | 7-dehydro-2-ME2 | 2-ME2-15$\alpha$, 16$\alpha$ |
|---|---|---|---|---|---|
| HUVEC Proliferation | 0.70 ± 0.11 | 0.72 ± 0.02 | 0.049 ± 0.00 | 4.39 ± 0.37 | 11.93 ± 2.17 |
| HUVEC invasion | 1.99 ± 0.39 | 2.07 ± 0.08 | 0.30 ± 0.02 | ND | 16.01 ± 1.98 |

14-Dehydro-2-ME2 is more potent than 2-ME2, 15-dehydro-2-ME2 is equipotent with the parental compound, and 7-dehydro-2-ME2 and 2-ME2-15$\alpha$,16$\alpha$ are less potent.

A second assay was also used to evaluate the analogs for potential antiangiogenic activity. The complex process of endothelial cell invasion and migration are key events during angiogenesis. The ability of compounds to inhibit the invasion and migration of endothelial cells through a biological membrane matrix was evaluated. Specifically, the ability of the 2-ME2 analogs, 15-dehydro-2-ME2, 14-dehydro-2-ME2 and 2-ME2-15$\alpha$,16$\alpha$ to inhibit the invasion and migration of human umbilical vein endothelial cells (HUVEC) through Matrigel® basement membrane material and a PET membrane with 8 $\mu$m pores was evaluated.

inhibited HUVEC invasion. 14-Dehydro-2-ME2 was more than 6 times more potent than 2-ME2 in inhibiting HUVEC invasion. 15-Dehydro-2-ME2 was equipotent with 2-ME2, while 2-ME2-15$\alpha$,16$\alpha$ was less potent.

In Vivo Studies

The analogs were tested for antitumor activity using an MDA-MB-435 breast cancer xenograft model. Tumor fragments of MDA-MB-435 (30 mg) were implanted subcutaneously into female athymic NCr-nu mice (SWF-1) weighing approximately 24 g. The tumor fragments were harvested from nude mice hosts. Animal weight and tumor dimensions were measured twice weekly with calipers and tumor weights estimated using 2-dimensional measurements of length and width and the formula $[1 \times (w)^2]/2$. When the tumors reached an approximate size equivalent to 175 mg (13 days after implantation) the mice were randomized to treatment or control groups and treatments were begun. The compounds were administered intraperitoneally daily for 30 days on the basis of individual animal body weights. Treatment groups contained 10 mice and the vehicle treated control group consisted of 20 mice. The mean tumor burdens were plotted for each treatment group and compared to controls. The means of the tumor burden data were analyzed for differences using a one-sided Student's t-test, with a P<0.05 considered to be significant difference. Tumor growth delay, the difference between the time for the median of each group (treatment and control) to reach a tumor burden of 1500 mg was calculated.

The tumor burden was plotted versus time and the results shown in FIG. 4. All three analogs tested, 15-dehydro-2-ME2, 14-dehydro-2-ME2, and 2-ME2-15α,16α were superior to 2-ME2 in this trial. 2-ME2-15α,16α provided the longest tumor growth delay of 11.3 days. Similar effects were observed with 14-dehydro-2-ME2, which provided a 10.0-day growth delay of the tumor. The analog 15-dehydro-2-ME2 was slightly less effective, providing a 7.5-day tumor growth delay. Statistical analyses indicate statistically significant differences between the control tumors and 14-dehydro-2-ME2- and 2-ME2-15α,16α-treated tumors at days 16–43. Statistically significant differences were observed at days 16–26 and day 36 with 15-dehydro 2-ME2, but the differences between the control and treated groups were not statistically significant at the end of the trial. No adverse effects, as indicated by weight loss, were encountered during the trial with any of the compounds.

EXAMPLE 2

Methods of Synthesizing 2-Methoxyestradiol and 2-Methoxy-7α-Methylestradiol

The method according to the present invention of synthesizing 2-Methoxyestradiols (8a, 8b) is illustrated in FIG. 5 and is described in particularity below.

1. Estradiol Diacetate (2a)

Under nitrogen, acetic anhydride (50 mL, 264.5 mmol) was added to a solution of estradiol (1a) (20.0 g, 73.43 mmol) in dry pyridine (200 mL). The reaction mixture was stirred at room temperature overnight (16 h). The next morning, analysis by tlc (5% acetone/$CH_2Cl_2$) indicated a complete reaction. The mixture was cooled in an ice bath and the excess acetic anhydride quenched by addition of methanol (25 mL). The mixture was stirred at 0° C. for one hour and then allowed to warm to room temperature. The solvents were removed in vacuo and the solid residue crystallized from hot methanol to give the pure diacetate (2a) (24.87 g, 95%).

mp=127–128° C.

FTIR (KBr, diffuse reflectance) $v_{max}$ 2924, 2874, 1765 and 1734 $cm^{-1}$.

NMR (300 MHz, $CDCl_3$) δ 0.823 (s, 18-$CH_3$), 2.056 (s, 17-OAc), 2.277 (s, 3-OAc), 4.688 (dd, $J_1$=9.3 Hz, $J_2$=7.5 Hz, 17-H), 6.786 (d, J=2.7 Hz, 4-H), 6.834 (dd, $J_1$=8.55 Hz, $J_2$=2.7 Hz, 2-H), 7.275 (d, J=8.55 Hz, 1-H) ppm.

Analysis. Calc. for $C_{22}H_{28}O_4$: C, 74.13; H, 7.92. Found: C, 73.98, H, 7.99.

2. 7α-Methylestradiol Diacetate (2b)

Following the procedure outlined for the synthesis of (2a), 7α-methylestradiol (1b) (10.0 g, 34.91 mmol) was reacted with acetic anhydride (25 mL, 264.5 mmol) in dry pyridine (100 mL) to give the pure diacetate (2b) (11.57 g, 89.4%).

mp=143–144° C.

FTIR (KBr, diffuse reflectance) $v_{max}$ 2973, 2917, 2883, 1766 and 1734 $cm^{-1}$.

NMR (300 MHz, $CDCl_3$) δ 0.829 (s, 18-$CH_3$), 0.841 (d, J=7.2 Hz, 7-$CH_3$), 2.060 (s, 17-OAc), 2.276 (s, 3-OAc), 4.699 (dd, $J_1$=8.6 Hz, $J_2$=7.6 Hz, 17-H), 6.779 (d, J=2.4 Hz, 4-H), 6.842 (dd, $J_1$=8.33 Hz, $J_2$=2.4 Hz, 2-H), 7.287 (d, J=8.33 Hz, 1-H) ppm.

Analysis. Calc. for $C_{23}H_{30}O_4$: C, 74.56; H, 8.16. Found: C, 74.40; H, 8.13.

3. 2-Acetylestradiol 17-acetate (3a)

Under nitrogen, solid zirconium tetrachloride (60 g, 257.5 mmol) was added to a solution of the diacetate (2a) (20.0 g, 56.11 mmol) in dry dichloromethane (1.5 L). The suspension was stirred at room temperature for 48 h. At the end of that time, analysis by tlc (1% acetone in $CH_2Cl_2$) indicated a complete reaction. The brown-yellow suspension was cooled in an ice bath and quenched by the slow addition of water (250 mL) with stirring. The yellow mixture was stirred at 0° C. for one hour, diluted further with water (500 mL) and extracted with methylene chloride (3×). The organic extracts were washed with water (2×), filtered through anhydrous sodium sulfate, combined, and concentrated in vacuo to give 19.8 g crude product as a yellow solid. Crystallization of this material from hot methanol gave the pure product (3a) (16.8 g, 84%) as a light yellow solid.

mp=198–200° C.

FTIR (KBr, diffuse reflectance) $v_{max}$ 3231, 2924, 1727, 1642 and 1619 $cm^{-1}$.

NMR (300 MHz, $CDCl_3$) δ 0.844 (s, 18-$CH_3$), 2.069 (s, 17-OAc), 2.604 (s, 2-Ac), 4.703 (dd, $J_1$=9.3 Hz, $J_2$=7.5 Hz, 17-H), 6.693 (s, 4-H), 7.597 (s, 1-H), 12.041 (s, 3-OH) ppm.

Analysis. Calc. for $C_{22}H_{28}O_4$: C, 74.13; H, 7.92. Found: C, 74.02; H, 7.92.

4. 2-Acetyl-7α-methylestradiol 17-acetate (3b)

Following the procedure outlined for the synthesis of (3a), zirconium tetrachloride (33 g, 141.6 mmol) was added to a solution of the diacetate (2b) (11.0 g, 29.7 mmol) in dry dichloromethane (1 L). The suspension was stirred at room temperature for 48 h. At the end of that time, NMR analysis of a small aliquot taken to dryness indicated only ~33% reaction. Additional $ZrCl_4$ (33 g, 141.6 mmol) was added and the reaction was stirred at room temperature for an additional 3 days. At the end of that time, NMR analysis indicated a complete reaction. The reaction mixture was cooled in an ice bath, diluted with water (~200 mL) and stirred at 0° C. for one hour. The mixture was then extracted with dichloromethane (3×). The organic fractions were washed with water (2×), filtered through $Na_2SO_4$, combined and concentrated in vacuo to give 11.3 g crude product as a yellow foam. Crystallization of this material from hot methanol gave 7.0 g of a light yellow solid. The mother liquors were concentrated and purified via Flash column chromatography (methylene chloride) to give an additional 0.6 g product. Total yield (3b) (7.6 g, 69%).

mp=145–147° C.

FTIR (KBr, diffuse reflectance) $v_{max}$ 3230, 2948, 1726, 1640 and 1619 $cm^{-1}$.

NMR (300 MHz, $CDCl_3$) δ 0.840 (d, J=7.2 Hz, 7-$CH_3$), 0.852 (s, 18-$CH_3$), 2.070 (s, 17-OAc), 2.604 (s, 2-Ac), 4.712 (dd, $J_1$=9.45 Hz, $J_2$=7.65 Hz, 17-H), 6.684 (s, 4-H), 7.628 (s, 1-H), 12.003 (s, 3-OH) ppm.

Analysis Calc. for $C_{23}H_{30}O_4$: C, 74.56; H, 8.16. Found: C, 74.45; H, 8.10.

The use of zirconium tetrachloride in the Fries rearrangement was found to be superior to the use of other Lewis acid mediators such as aluminum chloride in that the reaction proceeds at ambient temperature and gives a much higher yield of product. When the Fries rearrangement is carried out using the conventional aluminum choride catalyst, the reaction yield is only 40–50% and the product mixture requires chromatographic purification to separate the product from the unreacted starting material. When zirconium tetrachloride is used in this reaction, the reaction yields range from 75–85% and the product can be purified by simple crystallization.

The synthetic methodology for the compositions of the invention represents a novel improvement over known procedures for the synthesis of 2-methoxyestradiol derivatives. In particular, application of the zirconium tetrachloride mediated Fries rearrangement for conversion of estradiol diacetate (2a) to the 2-acetyl derivated compounds (3a, 3b) is an efficient method for the selective functionalization of the 2-position of estradiol (Harrowven, D. C.; Dainty, R. F. "Zirconium tetrachloride as a Mediator for Ambient Temperature ortho-Fries Rearrangements", *Tetrahedron Lett.* 37, 7659–7660 (1996). Most previously known methods for such functionalizations give mixtures of the 2- and 4-isomers.

5. 2-Acetylestradiol 17-acetate 3-benzyl Ether (4a)

Under nitrogen, benzyl bromide (16 mL, 134.5 mmol) was added to a mixture of the 2-acetyl compound (3a) (16.0 g, 43.19 mmol) and anhydrous potassium carbonate (25 g, 180.9 mmol) in dry dimethylformamide (500 mL). The mixture was heated to 60° C. over the weekend (62 h). At the end of that time, analysis by tlc ($CH_2Cl_2$) indicated about a 75% completion of reaction Additional benzyl bromide (16 mL, 134.5 mmol) and potassium carbonate (25 g, 180.9 mmol) were added and the reaction heated at 60° C. for a further four hours. At the end of that time, analysis by tlc indicated a complete reaction.

The reaction mixture was cooled to room temperature, poured into ice water (~1.5 L) and stirred until the ice melted. The resulting precipitate was collected by filtration and washed well with water until the filtrate was neutral. The light yellow solid crude product was crystallized from methylene chloride/methanol to give the pure product (4a) (17.62 g, 91.4%) as a white solid.

mp=172–174° C.

FTIR (KBr, diffuse reflectance) $v_{max}$ 2936, 2920, 1730, 1663, and 1604 $cm^{-1}$.

NMR (300 MHz, $CDCl_3$) δ 0.823 (s, 18-$CH_3$), 2.059 (s, 17-OAc), 2.576 (s, 2t-Ac), 4.680 (dd, $J_1$=8.85 Hz, $J_2$=7.35 Hz, 17-H), 5.122 (s, benzyl $CH_2$), 6.735 (s, 4-H), 7.343–7.456 (m, benzyl aromatic), 7.708 (s, 1-H) ppm.

Analysis Calc. for $C_{29}H_{34}O_4$: C, 78.00; H, 7.67. Found: C, 77.80; H, 7.68.

6. 2-Acetyl-7α-methylestradiol 17-acetate 3-benzyl Ether (4b)

Following the procedure outlined for the synthesis of (4a), benzyl bromide (7 mL, 58.85 mmol) was added to a mixture of the 2-acetyl compound (3b) (7.0 g, 18.89 mmol) and anhydrous potassium carbonate (11 g, 79.6 mmol) in dry dimethylformamide (250 mL). The reaction mixture was then heated to 60° C. overnight. Analysis by tlc ($CH_2Cl_2$) indicated an incomplete reaction. Additional benzyl bromide (10 mL, 84.1 mmol) and potassium carbonate (11 g, 79.6 mmol) were added and the reaction continued for another 24 hours. Analysis by tlc at that time indicated a complete reaction. The reaction mixture was cooled to room temperature, filtered, diluted with water (~1 L) and extracted with dichloromethane (3×). The organic fractions were washed with water (2×), saturated sodium bicarbonate solution (1×), filtered through sodium sulfate, combined and concentrated in vacuo to give 15 g of a yellow oily solid. Crystallization of this material from hot methanol gave the pure benzyl ether (4b) (6.7 g, 77%).

mp=179–181° C.

FTIR (KBr, diffuse reflectance) $v_{max}$ 2927, 1734, 1663, and 1603 $cm^{-1}$.

NMR (300 MHz, $CDCl_3$) δ 0.832 (s, 18-$CH_3$), 0.842 (d, J=5.7 Hz, 7-$CH_3$), 2.060 (s, 17-OAc), 2.572 (s, 2-Ac), 4.694 (dd, $J_1$=9.16 Hz, $J_2$=7.95 Hz, 17-H), 5.117 (s, benzyl $CH_2$), 6.731 (s, 4-H), 7.335–7.459 (m, benzyl aromatic), 7.723 (s, 1-H) ppm.

Analysis Calc. for $C_{30}H_{36}O_4$: C, 78.23; H, 7.88. Found: C, 78.09; H, 7.90.

7. 2-Acetoxyestradiol 17-acetate 3-benzyl Ether (5a)

Under nitrogen, meta-chloroperbenzoic acid (77%, 17.0 g, 75 mmol) was added to a mixture of the 2-acetyl benzyl ether (4a) (17.4 g, 39 mmol) and disodium phosphate (14 g, 98 mmol) in methylene chloride (800 mL). The reaction mixture was stirred overnight at room temperature. After that time, analysis by tlc (2% acetone in $CH_2Cl_2$) indicated a complete reaction. The mixture was diluted with water (1 L) and extracted with methylene chloride (3×). The organic fractions were washed with water (1×), 10% $Na_2SO_3$ solution (1×) and 1/2 saturated sodium bicarbonate solution (1×), filtered through $Na_2O_4$, combined and concentrated in vacuo. The residue was crystallized from methanol to give the pure 2-acetoxy derivative (5a) (14.85 g, 82.4%) as a white crystalline solid.

mp=151–153° C.

FTIR (KBr, diffuse reflectance) $v_{max}$ 2929, 1758, 1733, and 1615 $cm^{-1}$.

NMR (300 MHz, $CDCl_3$) δ 0.818 (s, 18-$CH_3$), 2.054 (s, 17-OAc), 2.259 (s, 2-OAc), 4.682 (dd, $J_1$=8.85 Hz, $J_2$=7.65 Hz, 17-H), 5.039 (s, benzyl $CH_2$), 6.713 (s, 4-H), 6.957 (s, 1-H), 7.301–7.381 (m, benzyl aromatic) ppm.

Analysis Calc. for $C_{29}H_{34}O_5$: C, 75.30; H, 7.41. Found: C, 75.54; H, 7.49.

The mother liquors were concentrated in vacuo to give 3.12 g residue as a foam.

8. 2-Acetoxy-7α-methylestradiol 17-acetate 3-benzyl Ether (5b)

Following the procedure outlined for the synthesis of (5a), meta-chloroperbenzoic acid (77%, 6.5 g, 29 mmol) was added to a mixture of the 2-acetyl compound (4b) (6.5 g, 14.1 mmol) and disodium phosphate (4.2 g, 29.6 mmol) in dry dichloromethane (300 mL). The mixture was stirred overnight at room temperature, after which time, analysis by tlc (2% acetone in $CH_2Cl_2$) indicated a complete reaction. The reaction mixture was transferred to a separatory funnel and washed with 10% sodium sulfite solution (1×), water (1×) and 50% saturated sodium bicarbonate solution (1×). The organic fractions were filtered through sodium sulfate, combined and concentrated in vacuo to give 7.1 g of yellow foam. Crystallization of this material from methanol containing 1% water gave 5.47 g product as a white solid. The mother liquors were concentrated in vacuo and the residue purified via Flash chromatography (1% acetone in $CH_2Cl_2$) to give an additional 0.59 g of product. Total yield (5b) (6.06 g, 90%).

mp=127–128° C.

FTIR (KBr, diffuse reflectance) $v_{max}$ 2943, 1763, 1722, and 1615 $cm^{-1}$.

NMR (300 MHz, $CDCl_3$) δ 0.819 (s, 18-$CH_3$), 0.841 (d, J=7.2 Hz, 7-$CH_3$), 2.054 (s, 17-OAc), 2.253 (s, 2-OAc), 4.695 (dd, $J_1$=8.7 Hz, $J_2$=7.8 Hz, 17-H), 5.029 (dd, $J_1$=13.81 Hz, $J_2$=11.71 Hz, benzyl $CH_2$), 6.703 (s, 4-H), 6.965 (s, 1-H), 7.304–7.385 (m, benzyl aromatic) ppm.

9. 2-Hydroxyestradiol 3-benzyl Ether (6a)

Under nitrogen, a solution of sodium hydroxide (1 N, 100 mL, 100 mmol) was added to a solution of the diacetate (5a) (14.6 g solid+residue from mother liquors, assume 38.5 mmol). The mixture was heated to 60° C. for 2 h. At that time, analysis by tlc (5% acetone in $CH_2Cl_2$) indicated an incomplete reaction. Additional sodium hydroxide solution (100 mL, 100 mmol) was added and the reaction continued for an additional hour. Analysis by tlc at that time indicated a complete reaction. The mixture was cooled to room temperature and acetic acid (glacial, 8 mL, 139.2 mmol) was added. The mixture was diluted with water (1.5 L) and the resulting precipitate collected by filtration. After air drying, the solid was dissolved in methylene chloride, filtered through $Na_2SO_4$ and concentrated in vacuo to give 13.1 g crude product. Trituration of this material with ether gave the pure product (6a) (12.56 g, 86.2% from 4a).

mp=218–220° C.

FTIR (KBr, diffuse reflectance) $v_{max}$ 3524, 3280, 2919, and 1605 cm$^{-1}$.

NMR (300 MHz, CDCl$_3$) δ 0.776 (s, 18-CH$_3$), 3.728 (t, J=9.15 Hz, 17-H), 5.061 (s, benzyl CH$_2$), 5.464 (s, OH), 6.649 (s, 4-H), 6.905 (s, 1-H), 7.359–7.422 (m, benzyl aromatic) ppm.

Analysis Calc. for $C_{25}H_{30}O_3 \cdot 1/10H_2O$: C, 78.95; H, 8.00. Found: C, 79.09; H, 7.97.

10. 2-Hydroxy-7α-methylestradiol 3-benzyl Ether (6b)

Under nitrogen, a solution of sodium hydroxide (1 N, 30 mL, 30 mmol) was added to a solution of the diacetate (5b) in methanol (300 mL). The reaction mixture was stirred at room temperature and monitored by tlc (2% acetone in $CH_2Cl_2$) which indicated an incomplete reaction after two hours. Additional sodium hydroxide solution (30 mL) was added and the reaction was heated to 60° C. Analysis by tlc indicated a complete reaction after one hour. The mixture was allowed to cool to room temperature and then concentrated in vacuo. The residue was diluted with water and the solution was adjusted to a pH of ~5 (pH paper) with glacial acetic acid. The resulting precipitate was collected by filtration, washed well with water and air-dried to give 5.1 g light purple solid. This material was dissolved in ethyl acetate (~300 mL), dried over sodium sulfate, filtered through Celite® and concentrated in vacuo. The residue was crystallized from ether/heptane to give the pure diol (6b) (4.5 g, 92%) as a light purple solid.

mp=146.5–147.5° C.

FTIR (KBr, diffuse reflectance) $v_{max}$ 3514, 2955, 2902 and 1607 cm$^{-1}$.

NMR (300 MHz, CDCl$_3$) δ 0.777 (s, 18-CH$_3$), 0.831 (d, J=7.5 Hz, 7-CH$_3$), 3.739 (m, 17-H), 5.053 (dd, J$_1$=13.1 Hz, J$_2$=10.96 Hz, benzyl CH$_2$), 6.636 (s, 4-H), 6.904 (s, 1-H), 7.351–7.425 (m, benzyl aromatic) ppm.

Analysis Calc. for $C_{26}H_{32}O_3 \cdot 1/10H_2O$: C, 79.19; H, 8.23. Found: C, 79.05; H, 8.13.

11. 2-Methoxyestradiol 3-benzyl Ether (7a)

Under nitrogen, solid lithium hydroxide monohydrate (1.4 g, 32.7 mmol) and dimethyl sulfate (2.8 mL, 29.59 mmol) were added to a solution of the diol (6a) (10.0 g, 26.42 mmol) in dry THF (150 mL). The reaction mixture was heated to reflux and monitored by TLC (3% acetone in $CH_2Cl_2$) which indicated a complete reaction after 3 h. The mixture was cooled to room temperature and solvents removed in vacuo. The residue was taken up in methylene chloride and washed with water (2x) and brine (1x). The organic fractions were filtered through $Na_2SO_4$, combined and concentrated in vacuo to give 10.2 g of a foam. Crystallization of this material from benzene/ether gave the pure product (7a) (9.61 g, 92.7%).

mp=113–114° C.

FTIR (KBr, diffuse reflectance) $v_{max}$ 3318, 2925, 2862, and 1606 cm$^{-1}$.

NMR (300 MHz, CDCl$_3$) δ 0.784 (s, 18-CH$_3$), 3.733 (t, J=8.7 Hz, 17-H), 3.861 (s, OCH$_3$), 5.104 (s, benzyl CH$_2$), 6.623 (s, 4-H), 6.851 (s, 1-H), 7.29–7.46 (m, benzyl aromatic) ppm.

Analysis Calc. for $C_{26}H_{32}O_3$: C, 79.56; H, 8.22. Found: C, 79.37; H, 8.21.

12. 2-Methoxy-7α-methylestradiol 3-benzyl Ether (7b)

Following the procedure outlined for the synthesis of (7a), reaction of the diol (6b) (4.37 g, 11.13 mmol) with lithium hydroxide monohydrate (0.6 g, 14.01 mmol) and dimethylsulfate (1,1 mL, 11.6 mmol) in dry THF (60 mL) gave the pure 2-methoxy product (7b) (3.5 g, 77.3%) after crystallization from methanol/water.

mp=68–70° C.

FTIR (KBr, diffuse reflectance) $v_{max}$ 3415, 2953, and 1607 cm$^{-1}$.

NMR (300 MHz, CDCl$_3$) δ 0.783 (s, 18-CH$_3$), 0.818 (d, J=6.9 Hz, 7-CH$_3$), 3.745 (t, J=8.25 Hz, 17-H), 5.095 (s, benzyl CH$_2$), 6.607 (s, 4-H), 6.842 (s, 1-H), 7.292–7.464 (m, benzyl aromatic) ppm.

Analysis Calc. for $C_{27}H_{34}O_3 \cdot 1/10H_2O$: C, 79.41; H, 8.44. Found: C, 79.44; H, 8.52.

13. 2-Methoxyestradiol (8a)

A mixture of the 3-benzyl ether (7a) (1.0 g, 2.55 mmol) and 5% palladium on charcoal (1.0 g) in ethanol (50 mL) was hydrogenated in a Parr® shaker apparatus at 38 psi hydrogen pressure for 16 hours. The mixture was filtered through Celite® and concentrated in vacuo to give 0.72 g residue. Crystallization of this material from $CH_2Cl_2$/hexanes gave the pure product (8a) (0.65 g, 84.4%) as a white crystalline solid.

mp=183–185° C.

FTIR (KBr, diffuse reflectance) $v_{max}$ 3424, 3202, 2905, 2863, and 1607 cm$^{-1}$.

NMR (300 MHz, CDCl$_3$) δ 0.787 (s, 18-CH$_3$), 3.734 (t, J=8.1 Hz, 17-H), 3.858 (s, OCH$_3$), 5.433 (s, OH), 6.641 (s, 4-H), 6.795 (s, 1-H) ppm.

Analysis Calc. for $C_{26}H_{32}O_3 \cdot 2/7$ $CH_2Cl_2$: C, 70.99; H, 8.21. Found: C, 70.98; H, 8.22.

14. 2-Methoxy-7α-methylestradiol (8b)

Following the procedure outlined for the synthesis of (8a), a mixture of the benzyl ether (7b) (3.4 g, 8.36 mmol) in ethanol (100 mL) was hydrogenated over 5% Pd/C (3.4 g) in a Parr® shaker apparatus at a hydrogen pressure of 38 psi for 16 h. Filtration followed by concentration in vacuo gave 2.8 g solid residue. Crystallization of this material from methanol gave the pure 2-methoxy compound (8b) (2.25 g, 85%) as a white crystalline solid.

mp=159–161° C.

FTIR (KBr, diffuse reflectance) $v_{max}$ 3414, 3296, 2955, 2888 and 1608 cm$^{-1}$.

NMR (300 MHz, CDCl$_3$) δ 0.789 (s, 18-CH$_3$), 0.820 (d, J=6.9 Hz, 7-CH$_3$), 3.737 (t, J=8.25 Hz, 17-H), 4.769 (br. s., OH), 6.623 (s, 4-H), 6.789 (s, 1-H) ppm.

Analysis Calc. for $C_{20}H_{28}O_3$: C, 75.91; H, 8.92. Found: C, 76.05; H, 9.04.

EXAMPLE 3

Methods of Synthesizing 2-Methoxyestra-1,3,5(10), 15-tetraen-3,17β-diol (16)(15-dehydro-2-ME2)

The method according to the present invention of synthesizing 2-Methoxyestra-1,3,5(10),15-tetraen-3,17β-diol (16) (15-dehydro-2-ME2) is illustrated in FIG. 6 and is described in particularity below.

1. 2-Methoxyestrone 3-benzyl Ether (9)

A solution of the 17-alcohol (7a) (8.1 g, 20.64 mmol) in acetone (300 mL) was cooled to 0° C. in an ice bath and treated dropwise with Jones reagent with stirring until a yellow color persisted. At that point, the reaction mixture was stirred at 0° C. for another 5 m. and then was treated dropwise with isopropanol until a green color persisted. The resulting green suspension was diluted with water (500 mL) and extracted with methylene chloride (3×). The organic fractions were washed with water (1×), saturated sodium bicarbonate solution (1×) and brine (1×). The organic fractions were filtered through anhydrous sodium sulfate, combined and concentrated in vacuo. The residue was crystallized from methanol to give the pure product (9) (4.9 g, 60.8%).

m.p=154–156° C.

FTIR (KBr, diffuse reflectance) $v_{max}$ 2929, 1732 and 1605 cm$^{-1}$.

NMR (300 MHz, CDCl$_3$) δ 0.916 (s, 18-CH$_3$), 3.864 (s, 2-Ome), 5.111 (s, benzyl CH$_2$), 6.638 (s, 4-H), 6.842 (s, 1-H), 7.294–7.457 (m, benzyl aromatic) ppm.

Analysis Calc. for $C_{26}H_{30}O_3.1/5H_2O$: C, 79.24; H, 7.77. Found: C, 79.13; H, 7.76.

2. 17,17-Ethylenedioxy-2-methoxyestra-1,3,5(10)-trien-3-ol 3-benzyl Ether (10)

Under nitrogen, triethylorthoformate (3.8 mL, 22.8 mmol), ethylene glycol (2.5 mL, 44.8 mmol) and toluenesulfonic acid monohydrate (0.1 g, 0.53 mmol) were added to a solution of the 17-keto steroid (9) (3.5 g, 6.96 mmol) in methylene chloride (35 mL). The reaction mixture was stirred at room temperature for 16 h. After that time, analysis by tlc (CH$_2$Cl$_2$) indicated a complete reaction. The reaction mixture was diluted with methylene chloride (100 mL) and washed with saturated sodium bicarbonate solution (1×), water (1×) and brine (1×). The organic fractions were filtered through anhydrous sodium sulfate, combined and concentrated in vacuo to give 3.8 g of a clear oil. This material was purified by Flash chromatography (CH$_2$Cl$_2$) followed by crystallization from methanol to give the pure 17-ketal (10) (3.28 g, 84.2%).

m.p=87–88° C.

FTIR (KBr, diffuse reflectance) $v_{max}$ 2940, and 1606 cm$^{-1}$.

NMR (300 MHz, CDCl$_3$) δ 0.885 (s, 18-CH$_3$), 3.862 (s, 2-Ome), 3.887–3.981 (m, ketal CH$_2$'s) 5.100 (s, benzyl CH$_2$), 6.620 (s, 4-H), 6.849 (s, 1-H), 7.286–7.459 (m, benzyl aromatic) ppm.

Analysis Calc. for $C_{28}H_{34}O_4$: C, 77.39; H, 7.89. Found: C, 77.10; H, 7.86.

3. 17,17-Ethylenedioxy-2-methoxyestra-1,3,5(10)-trien-3-ol (11)

Under nitrogen, ammonium formate (0.5 g, 7.9 mmol) and palladium on charcoal (10%, 0.5 g) were added to a solution of the 3-benzyl ether (10) (0.5 g, 1.15 mmol) in methanol (10 mL) and THF (5 mL). The reaction mixture was then stirred overnight at room temperature. After that time, analysis by tlc (CH$_2$Cl$_2$) indicated a complete reaction. The mixture was diluted with methylene chloride (50 mL), filtered through Celite®, and concentrated in vacuo. The residue was taken up in methylene chloride, washed with water (2×) and brine (1×), filtered through anhydrous sodium sulfate, combined and concentrated in vacuo. The residue was crystallized from methanol to give the pure product (11) (0.33 g, 83.3%).

m.p=150–151° C.

FTIR (KBr, diffuse reflectance) $v_{max}$ 3441, 2932, and 1619 cm$^{-1}$.

NMR (300 MHz, CDCl$_3$) δ 0.889 (s, 18-CH$_3$), 3.849 (s, 2-Ome), 3.881–3.975 (m, ketal CH$_2$'s), 5.531 (br. s, OH), 6.631 (s, 4-H), 6.787 (s, 1-H) ppm.

Analysis Calc. for $C_{21}H_{28}O_4.1/10$ MeOH: C, 72.90; H, 8.23. Found: C, 72.77; H, 8.09.

4. 17,17-Ethylenedioxy-2-methoxyestra-1,3,5(10)-trien-3-ol Acetate (12)

Under nitrogen, acetic anhydride (25 mL, 265 mmol) was added to a solution of the ketal (11) (4.5 g, 13.06 mmol) in dry pyridine (25 mL, 310 mmol). The reaction was stirred overnight at room temperature in the dark. After that time, methanol (50 mL) was added and solvents removed in vacuo. The treatment with methanol was repeated and the residue obtained crystallized from methanol to give the pure 3-acetate (12) (4.85 g, 96%).

m.p=166–167° C.

FTIR (KBr, diffuse reflectance) $v_{max}$ 2933, 1765 and 1615 cm$^{-1}$.

NMR (300 MHz, CDCl$_3$) δ 0.885 (s, 18-CH$_3$), 2.299 (s, OAc), 3.801 (s, 2-Ome), 3.884–3.983 (m, ketal CH$_2$'s), 6.731 (s, 4-H), 6.895 (s, 1-H) ppm.

Analysis Calc. for $C_{23}H_{30}O_5.1/6$ MeOH: C, 71.01; H, 7.89. Found: C, 71.04; H, 7.81.

5. 17,17-Ethylenedioxy-16α-bromo-2-methoxyestra-1,3,5 (10)-trien-3-ol Acetate (13)

Under nitrogen, solid phenyltrimethylammonium tribromide (4.92 g, 13 mmol) was added to a solution of the 3-acetate (12) (4.6 g, 11.9 mmol) in dry THF (100 mL) cooled to −5° C. in an ice-salt bath. The reaction was stirred at 2° C. overnight. After that time, saturated sodium bicarbonate solution (50 mL) was added and the mixture was extracted with ethyl acetate (3×). The organic fractions were washed with saturated sodium bicarbonate solution (2×), sodium thiosulfate solution (10%, 1×), and ice-cold water (3×). The organic fractions were dried over sodium sulfate, filtered and concentrated in vacuo to give 6.5 g residue. This material was crystallized from methanol to give the pure 16-bromo compound (13) (2.97 g, 54%).

m.p=210–212° C.

FTIR (KBr, diffuse reflectance) $v_{max}$ 2918, 1766 and 1616 cm$^{-1}$.

NMR (300 MHz, CDCl$_3$) δ 0.919 (s, 18-CH$_3$), 2.296 (s, OAc), 3.797 (s, 2-Ome), 3.921–4.314 (m, ketal CH$_2$'s), 4.551 (dd, $J_1$=10.4 Hz, $J_2$=4.4 Hz, 16-H), 6.727 (s, 4-H), 6.870 (s, 1-H) ppm.

Analysis Calc. for $C_{23}H_{29}BrO_5$: C, 59.36; H, 6.28. Found: C, 59.51; H, 6.30.

6. 17,17-Ethylenedioxy-2-methoxyestra-1,3,5(10),15-tetraen-3-ol Acetate (14)

Under argon, freshly cut potassium metal (0.77 g, 19.7 mmol) was added to tert-butanol (33 mL) and the mixture heated to reflux until all of the metal had reacted. The mixture was cooled slightly and the excess tert-butanol was removed under a slight vacuum. Xylene (70 mL) was added and distilled off three times followed by a fourth addition of xylene (70 mL). A solution of the 16-bromo compound (13) 1.07 g, 2.3 mmol) in dry xylene (100 mL) was concentrated to 50 mL to remove any moisture. After cooling to room temperature, the steroid solution was added to the potassium t-butoxide solution and the mixture heated to reflux for 17 hours. The reaction mixture was cooled to room temperature, poured into water, and extracted with ethyl acetate (3×). The organic fractions were washed with water (3×), combined, dried over sodium sulfate, filtered and concentrated in vacuo to give 1.01 g residue. This material was dissolved in benzene and filtered through a small Florisil column. The eluate was concentrated in vacuo to give 0.73 g residue. This material was crystallized from methanol to give the pure tetraene (14) (0.64 g, 87%)

m.p=161–162° C.

FTIR (KBr, diffuse reflectance) $v_{max}$ 3432, 2935, 2900, and 1619 cm$^{-1}$.

NMR (300 MHz, CDCl$_3$) δ 0.972 (s, 18-CH$_3$), 3.868 (s, 2-OMe), 3.962–4.030 (m, ketal CH$_2$'s), 5.434 (s, OH), 5.752 (dd, $J_1$=6.2 Hz, $J_2$=3.4 Hz, 15-H), 6.263 (dd, $J_2$=6.2 Hz, $J_2$=1.2 Hz, 16-H), 6.653 (s, 4-H), 6.790 (s, 1-H) ppm.

Analysis Calc. for $C_{21}H_{26}O_4 \cdot 1/2MeOH$: C, 72.04; H, 7.87. Found: C, 72.16; H, 7.78.

7. 2-Methoxyestra-1,3,5(10),15-tetraen-3-ol-17-one (15)

Under nitrogen toluenesulfonic acid monohydrate (0.1 g, 0.53 mmol) was added to a solution of the 17-ketal (14) (1.88 g, 5.5 mmol) in acetone (120 mL) and water (20 mL). The reaction mixture was stirred at room temperature for 1.5 h, diluted with cold water (150 mL), and extracted with benzene (3×). The organic fractions were washed with saturated sodium bicarbonate solution (2×) and brine (3×), dried over anhydrous sodium sulfate, filtered and concentrated in vacuo to give 1.78 g residue. This material was purified by chromatography followed by crystallization from methylene chloride/hexanes to give the pure 17-ketone (15, 1.05 g, 64%)

m.p=212–214° C.

FTIR (KBr, diffuse reflectance) $v_{max}$ 3332, 2930, and 1696 cm$^{-1}$.

NMR (300 MHz, CDCl$_3$) δ 1.120 (s, 18-CH$_3$), 3.872 (s, 2-Ome), 5.464 (s, OH), 6.092 (dd, $J_1$=6.0 Hz, $J_2$=3.2 Hz, 16-H), 6.6783 (s, 4-H), 6.789 (s, 1-H), 7.636 (dd, $J_1$=6.0 Hz, $J_2$=1.1 Hz, 15-H) ppm.

Analysis Calc. for $C_{19}H_{22}O_3$: C, 76.48; H, 7.43. Found: C, 76.42; H, 7.27.

8. 2-Methoxyestra-1,3,5(10),15-tetraen-3,17β-diol (16) (15-dehydro-2-ME2)

Under nitrogen, solid lithium aluminum hydride (0.15 g, 3.95 mmol) was added to a solution of the 17-ketone (15) (0.06 g, 0.2 mmol) in dry ether (60 mL) cooled to −5° C. in an ice-salt bath. The reaction was stirred at −5° C. for one hour then quenched cautiously with dropwise addition of water. The mixture was neutralized with 5% $H_2SO_4$, diluted with water and extracted with ethyl acetate (3×). The organic fractions were washed with saturated sodium bicarbonate solution (2×) and water (3×), combined, dried over sodium sulfate, filtered and concentrated in vacuo to give 0.073 g residue. This material was triturated with ether to give the pure 17-ol (16) (0.055 g, 91%).

m.p=191–193° C.

FTIR (KBr, diffuse reflectance) $v_{max}$ 3506, 3241, 2938, and 1607 cm$^{-1}$.

NMR (300 MHz, CDCl$_3$) δ 0.886 (s, 18-CH$_3$), 3.862 (s, 2-Ome), 4.403 (br.s, 17-H), 5.446 (s, OH), 5.718 (ddd, $J_1$=5.9 Hz, $J_2$=3.3 Hz, $J_3$=1.1 Hz, 16-H), 6.032 (m, 15-H), 6.656 (s, 4-H), 6.788 (s, 1-H) ppm.

Analysis Calc. for $C_{19}H_{24}O_3 \cdot 1/3H_2O$: C, 74.49; H, 8.11. Found: C, 74.35; H, 8.05.

EXAMPLE 4

Methods of Synthesizing Compounds of Formula I

The method according to the present invention of synthesizing compounds of the Formula I is described in particularity below.

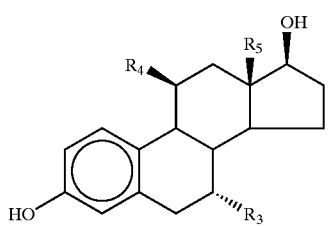

General Formula V

An estradiol of General Formula V can be converted to the corresponding 3,17-diacetate derivative by using standard methods, e.g. by reaction with acetic anhydride in pyridine (Greene, T. W. et al., *Protective Groups in Organic Synthesis*, 3$^{rd}$ edition, John Wiley & Sons, Inc., p. 150 (1999)). Then the diacetate is subjected to a Fries rearrangement to give the 2-acetyl 17-acetate derivative. For this reaction, several methodologies are known in the art (Gerecs, A., In *Friedel-Crafts and Related Reactions*, Olah, G. A. Ed.; Interscience: New York, Vol. III, Pt. 1, p. 499 (1964)). The most preferred method uses Zirconium tetrachloride in methylene chloride (Harrowven, D. et al., *Tetrahedron Lett.*, 37, p. 7659 (1996)). The 2-acetylestra-1,3, 5(10)-trien-3,17β-diol 17-acetate thus obtained can then be converted to a 3-benzyl ether by reaction with benzyl bromide and potassium carbonate in dimethylformamide (Green, supra, p. 266). Other appropriate protective groups for the 3-hydroxy include protection as the methoxymethyl ether (Green, supra, p. 257) or the methoxyethoxymethyl ether (Green, supra, p. 258).

The 2-acetylestra-1,3,5(10)-trien-3,17β-diol 17-acetate 3-benzyl ether thus obtained is subjected to a Baeyer-Villeger oxidation with meta-chloroperbenzoic acid in methylene chloride (Hudlický, M., *Oxidations in Organic Chemistry*, ACS Monograph 186, Washington, D.C., pp. 186–195 (1990); Krow, G. R. *Org. Reac.* 43, p. 251 (1993)) to give the 2-acetoxyestra-1,3,5(10)-trien-3,17β-diol 17-acetate 3-benzyl ether. Alternative reagents for this transformation include selenium catalyzed oxidation with aqueous hydrogen peroxide (Brink, G-J. et al., *J. Org Chem.* 66, p. 2429 (2001)), and acid-catalyzed hydrogen peroxide oxidation in 1,1,1,3,3,3-hexafluoro-2-propanol (Berkessel, A. et al., *Tetrahedron Lett.* 42, p. 2293 (2001)). Base hydrolysis of the 2,17-diacetate thus obtained then gives the appropriate estra-1,3,5(10)-trien-2,3,17β-triol 3-benzy ether. Conversion of this material to the corresponding 2-alkoxy derivative can be selectively carried out by reaction with a dialkylsulfate and lithium hydroxide monohydrate in tetrahydrofuran (Basak, A. et al., *Tetrahedron Lett.* 39, p. 4883 (1998)). An alternative method for selectively obtaining the 2-alkoxyderivative is reaction with the corresponding alkyl bromide in the presence of potassium carbonate in acetone (Prokai, L. et al., *J. Med. Chem.* 44, p. 110 (2001)).

The 2-alkoxyestra-1,3,5(10)-trien-3,17β-diol 3-benzyl ether derivative thus obtained is then oxidized to produce the corresponding 2-alkoxyestra-1,3,5(10)-trien-3-ol-17-one 3-benzyl ether derivative. For this reaction, several methodologies are known in the art (Hudlicky, supra; Fried et al., supra; Acosta, C. K. et al., *Steroids* 58, pp. 205–208 (1993)). Replacement of the 3-benzyl ether protecting group with a 3-acetate is then carried out using catalytic transfer hydrogenation (Prokai et al., supra) followed by reaction with acetic anhydride in pyridine. The 2-alkoxy-3-acetoxyestra-1,3,5(10)-trien-17-one derivative thus obtained can be brominated directly, for instance by reaction with copper(II) bromide in benzene/methanol (Segaloff, A. et al., *Steroids* 22, p. 99 (1973)). The 2-alkoxy-3-acetoxyestra-1,3,5(10)-trien-17-one derivative can also be converted to the enol acetate and then treated with bromine (Johnson, W. S. et al., *J. Am. Chem. Soc.* 79, p. 2005 (1957)), or to the enol silyl ether followed by reaction with e.g. N-bromosuccinimide (Heathcock, C. H. et al., *J. Am. Chem. Soc.* 104, p. 6081 (1982)). Dehydrobromination of the 16α-bromoketone, e.g. by reaction with LiBr/Li$_2$CO$_3$/DMF (Bull, J. R. et al., *J. Chem Soc., Perkin Trans. I*, p. 241 (1990)), usually results in a mixture of the 2-alkoxy-3-acetoxyestra, 3,5(10),15-tetraen-17-one and the 2-alkoxy-3-acetoxyestra,3,5(10),14-tetraen-17-one derivatives. These derivatives can be separated, whereafter the former is reduced to the corresponding 2-alkoxyestra-1,3,5(10),15-tetraen-17β-ol derivative by use of sodium borohydride, lithium aluminum hydride or other reducing systems.

The 2-alkoxyestra-1,3,5(10)-trien-3-ol-17-one 3-benzyl ether derivative can also be converted to the corresponding 17-cyclic 1,2-ethanediyl acetal. Replacement of the 3-benzyl ether with the 3-acetoxy functionality as described above followed by bromination gives a 16α-bromo-2-alkoxy-3-acetoxyestra-1,3,5(10)-trien-17-one cyclic 1,2-ethanediyl acetal derivative. Bromination can be accomplished using pyridinium tribromide, phenyltrimethylammonium tribromide or other brominating agents known in the art (Rasmusson, G. H. et al., *Steroids* 22, p. 107 (1973)). The 16α-bromo compound is dehydrobrominated and hydrolyzed to the 3-phenol by reaction with a base, e.g. potassium tert-butoxide in xylene or dimethyl sulfoxide, to give the $\Delta^{15}$ compound (Johnson, supra; Poirier, D. et al., *Tetrahedron* 47, p. 7751 (1991)). Mild hydrolysis of the ethylene ketal, for instance by treatment with p-toluenesulfonic acid in a mixture of acetone and water (Johnson, supra), results in a 2-alkoxyestra-1,3,5(10), 15-tetraen-3-ol-17-one compound. Reduction of this material to the corresponding (17β)-2-alkoxyestra-1,3,5(10),15-tetraen-17-ol derivative is then carried out as described above.

Additional methods to introduce a $\Delta^{15}$ double bond include: conversion of a 2-alkoxyestra-1,3,5(10)-trien-3-ol-17-one derivative to the 17-enol acetate and reaction with a palladium(II) salt (Takahashi, T. et al., *Tetrahedron* 41, p. 5747 (1985)), or reactions of the 17-enolate with methyl 2-pyridinesulfinate (Dionne, P. et al., *Steroids* 62, p. 674 (1997)).

Compounds of Formula I wherein $R_6$ is NOR, (H, OR), or (H, $OSO_2NHR$) with R being hydrogen, ($C_{1-6}$) alkyl or ($C_{1-6}$) acyl are obtained by using methods known in the art, from compounds of general formula I in which $R_6$ is oxo or OH.

Compounds of Formula I wherein $R_2$ is $SO_2NHR$, with R being hydrogen or ($C_{1-6}$) alkyl may be conveniently prepared from the corresponding 3-OH,17-oxo compounds by reaction with the analogous $RHNSO_2Cl$ and a sterically hindered pyridine base (Schwarz, S. et al. *Steroids* 61, p. 710 (1996)). Reduction of the 17-oxo-3-yl sulfamate thus obtained to the corresponding 17β-ol derivative is then carried out by reaction with sodium borohydride.

EXAMPLE 5

Synthesis of 2-Methoxyestra-1,3,5(10),14-tetraen-3,17β-diol (18)(14-dehydro-2-ME2)

The method according to the present invention of synthesizing 2-Methoxyestra-1,3,5(10),14-tetraen-3,17β-diol (18) (14-dehydro-2-ME2) is illustrated in FIG. 7 and is described in particularity below.

1. 2-Methoxy-3,17-diacetoxyestra-1,3,5(10),14,16-pentaene (17)

Under nitrogen, toluenesulfonic acid monohydrate (0.1 g, 0.53 mmol) was added to a solution of 2-Methoxyestra-1,3,5(10),15-tetraen-3-ol-17-one prepared in Example 3 (0.25 g, 0.84 mmol), isopropenyl acetate (5 mL, 45.15 mmol) and acetic anhydride (5 mL, 53 mmol) and the mixture was heated to reflux for 6 h. At the end of that time, analysis by tlc (2% acetone in $CH_2Cl_2$) indicated a complete reaction. The reaction was cooled to room temperature, poured into ice water (~100 mL) and stirred for 1 h. The mixture was extracted with methylene chloride (3×). The organic fractions were washed with water (1×), saturated sodium bicarbonate solution (1×) and water (1×), filtered through anhydrous sodium sulfate, combined and concentrated in vacuo. The residue was crystallized from methanol to give the pure diacetate (17) (0.259 g, 80.8%).

m.p=191–194° C.

FTIR (KBr, diffuse reflectance) $v_{max}$ 2931, 1763 and 1615 $cm^{-1}$.

NMR (300 MHz, $CDCl_3$) δ 1.105 (s, 18-$CH_3$), 2.233 (s, OAc), 2.309 (s, OAc), 3.809 (s, 2-OMe), 5.865 (dd, $J_1$=2.6 Hz, $J_2$=1.5 Hz, 15-H), 6.164 (d, J=2.6 Hz, 16-H), 6.785 (s, 4-H), 6.895 (s, 1-H) ppm.

Analysis Calc. for $C_{23}H_{26}O_5$.1/20MeOH: C, 72.09; H, 6.88. Found: C, 72.02; H, 6.81.

2. 2-Methoxyestra-1,3,5(10),14-tetraen-3,17β-diol (18) (14-dehydro-2-ME2)

A solution of the diacetate (17) (0.08 g, 0.21 mmol) in ethanol (5 mL) and THF (3 mL) was cooled to 0° C. in an ice bath. A solution of sodium borohydride (0.05 g, 1.32 mmol) in ethanol/water (10:3, 5 mL) was cooled to 0° C. in an ice bath and added to the steroid solution. The reaction mixture was stirred at 0° C. for 1 h., then allowed to warm to room temperature and stirred overnight. After that time, the reaction was diluted with water (20 mL) and neutralized with glacial acetic acid. The organic solvents were removed in vacuo under a stream of nitrogen, the residue was diluted with water (50 mL) and extracted with methylene chloride (3×). The organic fractions were washed with water (2×), brine (1×), filtered through sodium sulfate, combined and concentrated in vacuo. The residue was triturated with ether to give the pure product (18) (0.035 g, 55.7%).

m.p=169–171° C.

FTIR (KBr, diffuse reflectance) $v_{max}$ 3499, 3185, 2920, and 1606 $cm^{-1}$.

NMR (300 MHz, $CDCl_3$) δ 1.023 (s, 18-$CH_3$), 3.864 (s, 2-Ome), 4.101 (t, J=8.4 Hz), 5.210 (m, 15-H), 6.663 (s, 4-H), 6.813 (s, 1-H) ppm.

Analysis Calc. for $C_{19}H_{24}O_3$.2/5$H_2O$: C, 74.19; H, 8.13. Found: C, 74.04; H, 8.01.

EXAMPLE 6

Synthesis of Compounds of Formula II

The method according to the present invention of synthesizing compounds of Formula II is described in particularity below.

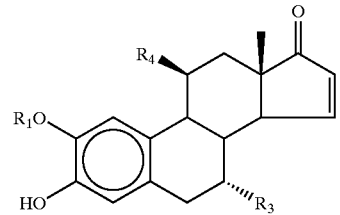

General Formula VI

A convenient starting material for the preparation of compounds of Formula II wherein $R_1$–$R_6$ have the previously given meaning is for instance an appropriately substituted 2-alkoxyestra-1,3,5(10),15-tetraen-3-ol-17-one of General Formula VI, whose synthesis is described above.

A possible synthesis route is as follows. An estradiol of General Formula VI can be converted to the corresponding 2-alkoxyestra-1,3,5(10),14,16-pentaen-3,17-diol diacetate by acid-catalyzed reaction with acetic anhydride, isopropenylacetate or other acylating agents (Rasmusson, supra; Bull, supra). The diacetate is treated with sodium borohydride or other reducing agents (Rasmusson, supra) to result in the formation of a 2-alkoxyestra-1,3,5(10),15-tetraen-3,17β-diol derivative. Optionally, a 2-alkoxyestra-1,3,5(10), 15-tetraen-3-ol-17-one cyclic 1,2-ethanediyl acetal can be converted by acid-catalyzed isomerization into the corresponding $\Delta^{14}$ derivative (Ponsold, K. et al., *J. Prakt. Chem.* 323, p. 819 (1981)). Removal of the acetal and reduction of the 17-oxo function produces the 2-alkoxyestra-1,3,5(10), 15-tetraen-3,17β-diol derivative. Compounds of general formula XVI can also undergo acid-catalyzed isomerization to give a mixture of the $\Delta^{15}$ and $\Delta^{14}$ derivatives. Separation followed by reduction of the $\Delta^{14}$ derivative gives the desired compound.

Compounds of Formula II wherein $R_2$ is $SO_2NHR$, with R being hydrogen or $(C_{1-6})$ alkyl may be conveniently prepared from the corresponding 3-OH,17-oxo compounds by reaction with the analogous $RHNSO_2Cl$ and a sterically hindered pyridine base (Schwarz, S. et al., *Steroids* 61, p. 710 (1996)). Reduction of the 17-oxo-3-yl sulfamate thus obtained to the corresponding 17β-ol derivative is then carried out by reaction with sodium borohydride.

EXAMPLE 7

Synthesis of 2-Methoxyestra-1,3,5(10),7-tetraen-3, 17β-diol (20)(7-dehydro-2-ME2)

The method according to the present invention of synthesizing 2-Methoxyestra-1,3,5(10),7-tetraen-3,17β-diol (20) (7-dehydro-2-ME2) is illustrated in FIG. 8 and is described in particularity below.

1. 2-Methoxyestra-1,3,5(10),7-tetraen-3,17β-diol (20)(7-dehydro-2-ME2)

Under nitrogen, a solution of L-Selectride in THF (1 M, 0.081 mL, 0.081 mmol) was added dropwise to a solution of 2-methoxy-3-hydroxyestra-1,3,5(10),7-tetraen-17-one (19) (0.008 g, 0.027 mmol) in dry THF (1.0 mL) cooled to 0° C. in an ice bath. The reaction was allowed to warm to room temperature and stirred for 45 in. Methanol (3 drops) followed by methanolic KOH (3%, 3 drops) were added and the mixture was cooled to 0° C. in an ice bath. Hydrogen peroxide solution (30%, 5 drops) was added and the mixture was allowed to warm to room temperature. The reaction was diluted with water, acidified with HCl, and extracted with methylene chloride (3×). The organic fractions were washed with water (1×) and brine (1×), filtered through sodium sulfate, combined and concentrated in vacuo to give 0.006 g residue. This material was crystallized from ether/hexanes to give the purified product (20) (0.0037 g, 45.9%).

NMR (300 MHz, CDCl$_3$) δ 0.662 (s, 18-CH$_3$), 3.376 (m, 17-H), 3.867 (s, 2-OMe), 5.402 (t, J=1.65 Hz, 7-H), 6.662 (s, 4-H), 6.692 (s, 1-H) ppm.

Analysis Calc. for $C_{19}H_{24}O_3$

EXAMPLE 8

Synthesis of Compounds of Formula III

The method according to the present invention of synthesizing compounds of Formula III is described in particularity below.

A convenient starting material for the preparation of compounds of Formula III wherein $R_1$–$R_6$ have the previously given meaning is for instance an appropriately substituted 2-alkoxyestra-1,3,5(10),6-tetraen-3-ol-17-one of General Formula VII, whose synthesis is described in the literature (Rao, P. N. et al., *Steroids* 49, p. 419 (1987)).

General Formula VII

Reduction of these compounds to the corresponding 2-alkoxyestra-1,3,5(10),6-tetraen-17β-ol derivatives are achieved by use of sodium borohydride, lithium aluminum hydride or other reducing systems.

Compounds of Formula III wherein $R_2$ is $SO_2NHR$, with R being hydrogen or $(C_{1-6})$ alkyl may be conveniently prepared from the corresponding 3-OH,17-oxo compounds by reaction with the analogous $RHNSO_2Cl$ and a sterically hindered pyridine base (Schwarz, S. et al., *Steroids* 61, p. 710 (1996)). Reduction of the 17-oxo-3-yl sulfamate thus obtained to the corresponding 17β-ol derivative is then carried out by reaction with sodium borohydride.

EXAMPLE 9

Synthesis of 2-Methoxyestra-1,3,5(10)trien-3,15α,16α17β-tetrol 16,17-acetonide (25a) (2-ME2-15α,16α) And 2-Methoxyestra-1,3,5(10)trien-3,15β,16β,17β-tetrol 16,17 Acetonide (25b)

The method according to the present invention of synthesizing 2-Methoxyestra-1,3,5(10)trien-3,15α,16α17β-tetrol 16,17-acetonide (25a) (2-ME2-15α,16α) and 2-Methoxycstra-1,3,5(10)trien-3,15 β,16β17β-tetrol 16,17 acetonide (25b) is illustrated in FIG. 9 and is described in particularity below.

1. 2-Methoxyestra-1,3,5(10),15-tetracn-3,17β-diol 17-acetate (21)

Under nitrogen, acetic anhydride (30 mL, 318 mmol) was added to a solution of 2-methoxyestra-1,3,5(10),15-3,17β-diol (16) (1.15 g, 3.83 mmol) in dry pyridine (35 mL 434 mmol). The reaction was stirred overnight at room temperature. Solvents were azeotropically removed in vacuo using benzene (2×). The residue was crystallized from methanol to give the pure diacetate. (21) (1.07 g, 72.4%).

m.p=164–165° C.

FTIR (KBr, diffuse reflectance) $v_{max}$ 2934, 1757, 1735 and 1613 cm$^{-1}$.

NMR (300 MHz, CDCl$_3$) δ 0.878 (s, 18-CH$_3$), 2.109 (s, 17-OAc), 2.302 (s, 3-OAc), 3.804 (s, 2-OMe), 5.382 (t, J=3.5 Hz, 17-H), 5.704 (ddd, J$_1$=6 Hz, J$_2$=3.2 Hz, J$_3$=1.4 Hz, 16-H), 6.091 (m, 15-H), 6.746 (s, 4-H), 6.876 (s, 1-H) ppm.

Analysis. Calc. for $C_{23}H_{28}O_5$.1/10MeOH: C, 71.57; H, 7.38. Found: C, 71.52; H, 7.46.

2. 3-Methoxyestra-1,3,5(10)-trien-3,15ξ,16ξ,17β-tetrol 3,17-diacetate (22)

Under nitrogen, a solution of the $\Delta^{15}$-steroid (21) (27.84 g, 72.4 mmol) in dry benzene (315 mL) was added to a solution of osmium tetroxide (20.5 g, 80.6 mmol) in benzene (520 mL) and pyridine (56 mL). The reaction was stirred mechanically at room temperature for 4 h, and then left without stirring at room temperature for 64 h. The reaction was diluted with benzene (510 mL) and methanol (940 mL). Aqueous solutions of potassium bicarbonate (123 g/720 mL) and sodium sulfite (123 g/720 mL) were added and the mixture was stirred at room temperature for 4 h. The reaction mixture was filtered and extracted with ethyl acetate (3×). The organic fractions were washed with cold brine (4×), combined, and concentrated in vacuo. Water was removed azeotropically in vacuo using benzene to give 32.3 g residue as crude product. This material was not characterized or further purified and was carried on to the next step.

3. 3-Methoxyestra-1,3,5(10)-trien-3,15α,16α,17β-tetrol Tetraacetate (23a) and 3-Methoxyestra-1,3,5(10)-trien-3, 15β,16β,17β-tetrol tetraacetate (23b)

Acetic anhydride (100 mL, 1.06 mol) was added to a solution of the crude mixture (22) (32.3 g, assume 72.4 mmol) in dry pyridine (100 mL, 1.24 mol) and the mixture was stirred overnight at room temperature. Solvents were removed in vacuo under a stream of nitrogen with solvent residues being removed azeotropically using methanol (2×) to give 37 g crude product. This material was combined with 39 g of crude product obtained from a separate batch to give a total amount of 67 g crude product as an isomer mixture. This material was resolved by stepwise crystallization (methanol) and dry column chromatography (ether) to give the pure 15α,16α-isomer (23a) (43.08 g, 59.2%).

m.p=168–171° C.

FTIR (KBr, diffuse reflectance) $v_{max}$ 2930, 1758, 1738 and 1613 cm$^{-1}$.

NMR (300 MHz, CDCl$_3$) δ 0.945 (s, 18-CH$_3$), 2.045 (s, OAc), 2.078 (s, OAc), 2.092 (s, OAc), 2.302 (s, 3-OAc), 3.799 (s, 2-OMe), 5.012 (d, J=6.6 Hz, 17-H), 5.160 (dd, J$_1$=14.7 Hz, J2=8.4 Hz, 15-H), 5.398 (dd, J$_1$=8.4 Hz, J$_2$=6.6 Hz, 16-H), 6.746 (s, 4-H), 6.876 (s, 1-H) ppm.

Analysis. Calc. for C$_{27}$H$_{34}$O$_9$: C, 64.53; H, 6.82. Found: C, 64.63; H, 6.84.

And the 15β,16β-isomer (23b, 11.78 g, 16.2%).

m.p=169–171° C.

FTIR (KBr, diffuse reflectance) $v_{max}$ 2939, 1743 and 1612 cm$^{-1}$.

NMR (300 MHz, CDCl$_3$) δ 1.093 (s, 18-CH$_3$), 2.031 (s, OAc), 2.058 (s, OAc), 2.064 (s, OAc), 2.306 (s, 3-OAc), 3.808 (s, 2-OMe), 4.724 (d, J=7.4 Hz, 17-H), 5.392 (t, J=6.3 Hz, 15-H), 5.498 (t, J=7.4 Hz, 16-H), 6.750 (s, 4-H), 6.876 (s, 1-H) ppm.

Analysis. Calc. for C$_{27}$H$_{34}$O$_9$: C, 64.53; H, 6.82. Found: C, 64.73; H, 6.80.

4. 3-Methoxyestra-1,3,5(10)-trien-3,15α,16α,17β-tetrol (24a)

Under nitrogen, a solution of potassium carbonate (6.0 g, 43.4 mmol) in water (330 mL) was added to a solution of the tetraacetate (23a) (10.0 g, 19.9 mmol) in methanol (1800 mL). The reaction mixture was stirred overnight at room temperature. Glacial acetic acid (5.2 mL, 90.48 mmol) was added and the solvents removed in vacuo. The residue was crystallized from methanol/water to give the purified tetrol (24a) (6.1 g, 91.7%).

m.p=228–230° C.

FTIR (KBr, diffuse reflectance) $v_{max}$ 3342, 2930, and 1589 cm$^{-1}$.

NMR (300 MHz, CDCl$_3$+D$_6$DMSO+D$_2$O) δ 0.812 (s, 18-CH$_3$), 3.520 (d, J=5.7 Hz, 17-H) 3.850 (s, 2-OMe), 3.940 (m, 15- and 16-H), 6.635 (s, 4-H), 6.783 (s, 1-H) ppm.

Analysis. Calc. for C$_{19}$H$_{26}$O5: C, 68.24; H, 7.84. Found: C, 68.29; H, 8.00.

5. 3-Methoxyestra-1,3,5(10)-trien-3,15β,16β,17β-tetrol (24b)

Following the same procedure given for the preparation of 24a, the tetraacetate (23b) (10.0 g, 19.9 mmol) in methanol (1800 mL) was hydrolyzed with potassium carbonate (6.0 g, 43.4 mmol) in water (330 mL) to give the pure tetrol (24b) (3.87 g, 58.2%).

m.p=224–225° C.

FTIR (KBr, diffuse reflectance) $v_{max}$ 3526, 3398, 3266, 2938, and 1621 cm$^{-1}$.

NMR (300 MHz, CDCl$_3$+D$_6$DMSO+D$_2$O) δ 0.925 (s, 18-CH$_3$), 3.420 (d, J=7.2 Hz, 17-H) 3.852 (s, 2-OMe), 4.123 (t, J=6.9 Hz, 16-H), 4.258 (dd, J1=6.9 Hz, J2=5.1 Hz, 15-H) 6.634 (s, 4-H), 6.794 (s, 1-H) ppm.

Analysis. Calc. for C$_{19}$H$_{26}$O$_5$.1/10MeOH: C, 67.95; H, 7.88. Found: C, 67.93; H, 7.79.

6. 3-Methoxyestra-1,3,5(10)-trien-3,15α,16α,17β-tetrol 15,16-acetonide (25a)

Under nitrogen, a solution of the tetrol (24a) (0.15 g, 0.45 mmol) in acetone (10 mL) was treated with perchloric acid (70%, 1 drop). The reaction was stirred at room temperature overnight. Analysis by tlc (5% acetone in CH$_2$Cl$_2$) indicated a complete reaction. The mixture was quenched with saturated sodium bicarbonate solution (1 mL) and solvent removed in vacuo under a stream of nitrogen. The residue was extracted with ethyl acetate (3×). The organic fractions were washed with saturated sodium bicarbonate solution (1×), water (1×) and brine (1×), combined, dried over sodium sulfate, filtered and concentrated in vacuo. The residue was crystallized from ether/hexanes to give the purified acetonide (25a) (0.16 g, 95%).

m.p=155–157° C.

FTIR (KBr, diffuse reflectance) $v_{max}$ 3534, 3208, 2934, and 1594 cm$^{-1}$.

NMR (300 MHz, CDCl$_3$) δ 0.888 (s, 18-CH$_3$), 1.323 (s, acetonide CH$_3$), 1.521 (s, acetonide CH$_3$), 3.775 (br. s, 17-H) 3.857 (s, 2-OMe), 4.429 (t, J=8 Hz, 16-H), 4.508 (dd, J$_1$=8 Hz, J$_2$=4.4 Hz, 15-H), 5.446 (s, OH), 6.653 (s, 4-H), 6.775 (s, 1-H) ppm.

Analysis. Calc. for C$_{22}$H$_{30}$O$_5$.1/4 hexane: C, 71.27; H, 8.53. Found: C, 71.35; H, 8.70.

7. 3-Methoxyestra-1,3,5(10)-trien-3,15β,16β,17β-tetrol 15,16-acetonide (25b)

Following the same procedure given for the preparation of 25a, the tetrol (24b) (0.1 g, 0.299 mmol) was reacted with perchloric acid (70%, 1 drop) in acetone (10 mL) overnight at room temperature. Identical workup gave after crystallization from ether/hexanes the pure acetonide (25b) (0.064 g, 57.2%).

m.p=188–191° C.

FTIR (KBr, diffuse reflectance) $v_{max}$ 3574, 3516, 2927, 1621 and 1594 cm$^{-1}$.

NMR (300 MHz, CDCl$_3$) δ 1.043 (s, 18-CH$_3$), 1.344 (s, acetonide CH$_3$), 1.515 (s, acetonide CH$_3$), 3.445 (m, 17-H) 3.855 (s, 2-OMe), 4.528 (t, J=6.1 Hz, 16-H), 4.640 (dd, J$_1$=6.1 Hz, J$_2$=4.5 Hz, 15-H), 5.439 (OH), 6.654 (s, 4-H), 6.777 (s, 1-H) ppm.

Analysis. Calc. for C$_{22}$H$_{30}$O$_5$ 1/5H$_2$O: C, 69.89; H, 8.10. Found: C, 69.88; H, 8.15.

EXAMPLE 10

Synthesis of Compounds of Formula IV

A convenient starting material for the preparation of compounds of Formula IV wherein R$_1$–R$_6$ have the previously given meaning is for instance an appropriately substituted 2-alkoxyestra-1,3,5(10),15-tetraen-3,17β-diol of Formula I whose synthesis is described above. Conversion of this material to the corresponding 3,17-diacetate followed by oxidation using osmium tetroxide yields a separable mixture of the 15α,16α- and 15β,16β-diols. Base hydrolysis of the 3,17-diacetate gives the corresponding 2-alkoxyestra-1,3,5(10)-trien-3,15,16,17β-tetrol derivative (Fishman, J. et al., *Tetrahedron Lett.*, p. 2929 (1967); Suzuki, E. et al., *Steroids* 60, p. 277 (1995)). Reaction of the thus obtained tetrol then gives the desired acetonide derivative.

Compounds of Formula IV wherein R$_2$ is SO$_2$NHR, with R being hydrogen or (C$_{1-6}$) alkyl may be conveniently prepared from the corresponding 3-OH,17-oxo compounds by reaction with the analogous RHNSO$_2$Cl and a sterically hindered pyridine base (Schwarz, S. et al., *Steroids* 61, p. 710 (1996)). Reduction of the 17-oxo-3-yl sulfamate thus obtained to the corresponding 17β-ol derivative is then carried out by reaction with sodium borohydride.

Equivalents

Those skilled in the art will be able to recognize, or be able to ascertain using no more than routine experimentation, many equivalents to the specific embodiments of the invention described herein. Such equivalents are intended to be encompassed by the following claims.

What is claimed is:

1. A compound represented by the following structural formula:

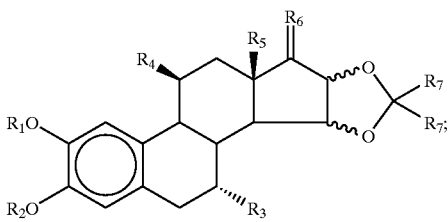

wherein:

$R_1$ is $(C_{1-6})$ alkyl, and optionally substituted by halogen;

$R_2$ is H, or $SO_2NHR$, with R being hydrogen or $(C_{1-6})$ alkyl;

$R_3$ is selected from the group consisting of hydrogen and $(C_{1-6})$ alkyl, and optionally substituted by halogen;

$R_4$ is hydrogen, $(C_{1-6})$ alkyl, $(C_{2-6})$ alkenyl, $(C_{2-6})$ alkynyl, aryl, or heteroary;

$R_5$ is $(C_{1-2})$alkyl;

$R_6$ is O, NOR, (H, OR), or (H, $OSO_2NHR$), wherein R is hydrogen, $(C_{1-6})$ alkyl or $(C_{1-6})$ acyl; and $R_7$ is hydrogen or $(C_{1-6})$ alkyl.

2. The compound of claim 1, wherein said compound is a pharmaceutically acceptable salt or ester thereof.

3. The compound of claim 1 or 2, wherein said compound in admixture with at least one pharmaceutically acceptable carrier, diluent, or excipient.

4. The compound of claim 3, wherein said carrier is a liposome.

5. The compound of claim 1, wherein said compound is a pure diasteriomer.

6. The compound of claim 1, wherein said compound is a mixture of diasteriomers.

7. A compound represented by the following structural formula:

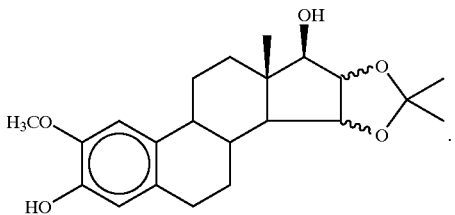

8. A method of inhibiting undesired cell proliferation, said method comprising contacting said cells or a tissue or organ in which proliferation of said cell is not desired, with a compound having the structure:

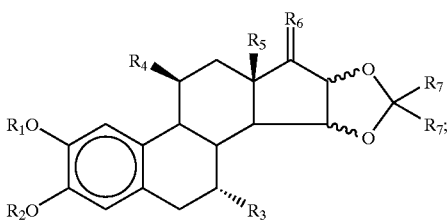

wherein:

$R_1$ is $(C_{1-6})$ alkyl, and optionally substituted by halogen;

$R_2$ is H, or $SO_2NHR$, with R being hydrogen or $(C_{1-6})$ alkyl;

$R_3$ is selected from the group consisting of hydrogen and $(C_{1-6})$ alkyl, and optionally substituted by halogen;

$R_4$ is hydrogen, $(C_{1-6})$ alkyl, $(C_{2-6})$ alkenyl, $(C_{2-6})$ alkynyl, aryl, or heteroary;

$R_5$ is $(C_{1-2})$alkyl;

$R_6$ is O, NOR, (H, OR), or (H, $OSO_2NHR$), wherein R is hydrogen, $(C_{1-6})$ alkyl or $(C_{1-6})$ acyl; and $R_7$ is hydrogen or $(C_{1-6})$ alkyl.

9. A method of inhibiting undesired cell proliferation, said method comprising contacting said cells or a tissue or organ in which proliferation of said cell is not desired, with a compound represented by the following structural formula:

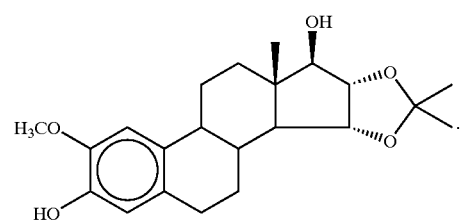

10. The method in accordance with claim 8 or 9, wherein said method further comprises administering said compound in a therapeutically effective amount in a pharmaceutically acceptable carrier.

11. The method in accordance with claim 10, wherein said undesired cell proliferation occurs in atherosclerosis.

12. The method in accordance with claim 10, wherein said undesired cell proliferation occurs in diabetic retinopathy, macular degeneration, or other ocular angiogenic disease.

13. The method in accordance with claim 10, wherein said undesired cell proliferation occurs in a fungal disease.

14. The method in accordance with claim 8 or 9, wherein said undesired cell proliferation results in the growth of a neoplasm.

15. The method in accordance with claim 14, wherein said neoplasm is selected from the group consisting of mammary, small-cell lung, non-small-cell lung, colorectal, leukemia, lymphoma, melanoma, pancreatic, renal, liver, myeloma, multiple mycloma, mesothelioma, central nervous system, ovarian, prostate, sarcoma of soft tissue or bone, head and neck, esophageal, stomach, bladder, retinoblastoma, squamous cell, testicular, vaginal, and neuroendocrine-related neoplasms.

16. The method in accordance with claim 14, wherein said neoplasm is cancerous.

17. The method in accordance with claim 8 or 9, wherein said undesired cell proliferation results in undesired angiogenesis.

18. The method in accordance with claim 8 or 9, wherein said undesired cell proliferation results in undesired microtubule formation and function.

19. The method in accordance with claim 10, wherein said compound is administered in combination therapy with other known chemotherapeutic or antineoplastic agents.

20. The method in accordance with claim 10, wherein said compound is administered via a pharmaceutically acceptable route.

21. The method in accordance with claim 10, wherein said compound is into biodegradable polymers for sustained release.

* * * * *

UNITED STATES PATENT AND TRADEMARK OFFICE
CERTIFICATE OF CORRECTION

PATENT NO.   : 6,852,710 B2
DATED        : February 8, 2005
INVENTOR(S)  : Rao et al.

It is certified that error appears in the above-identified patent and that said Letters Patent is hereby corrected as shown below:

Column 1,
Line 30, insert a period after the close parenthesis.
Line 37, replace "Includes" with -- includes --.

Column 5,
Line 33, replace "tetracn" with -- tetraen --.

Column 9,
Line 45, replace each occurrence of "mycloma" with -- myeloma --.

Column 10,
Line 52, replace "elasticum" with -- elasticurn --.

Column 12,
Line 53, replace "canrier" with -- carrier --.

Column 13,
Line 27, insert a period after the close parenthesis.

Column 17,
After Table 4, insert the following sentence: -- The $IC_{50}$ values for inhibition of proliferation and cell invasion were calculated from log dose response curves (n=3, mean $\pm$ SD). --

Column 18,
Line 27, delete the comma after "bovine".

Column 21,
Line 21, insert a period after "reaction".
Line 41, replace "2t-Ac" with -- 2-Ac --.
Line 64, replace "dichlioromethane" with -- dichloromethane --.

Column 22,
Line 25, replace "$Na_2\ O_4$" with -- $Na_2\ SO_4$ --.

Column 23,
Line 5, replace "(Sa)" with -- (5a) --.

UNITED STATES PATENT AND TRADEMARK OFFICE
CERTIFICATE OF CORRECTION

PATENT NO. : 6,852,710 B2
DATED : February 8, 2005
INVENTOR(S) : Rao et al.

It is certified that error appears in the above-identified patent and that said Letters Patent is hereby corrected as shown below:

Column 26,
Line 66, replace the second occurrence of "$J_2$" with -- $J_1$ --.

Column 27,
Line 3, replace "tetracn" with -- tetraen --.

Column 30,
Line 57, replace "tetracn" with -- tetraen --.
Line 60, replace "*Praki*" with -- *Prakt* --.

Column 31,
Line 24, replace "45 in" with -- 45 m --.

Column 32,
Line 15, replace "Methoxyestra" with -- Methoxyestra --.
Line 18, replace "tetracn" with -- tetraen --.

Column 33,
Line 6, replace "J2" with -- $J_2$ --.
Line 34, replace "O5" with -- $O_5$ --.

Column 35,
Line 19, replace "heteroary" with -- heteroaryl --.
Line 27, insert -- is -- before "in".
Line 49, replace "cell" with -- cells --.

Column 36,
Line 4, replace "heteroary" with -- heteroaryl --.
Line 12, replace "cell" with -- cells --.
Line 43, replace "mycloma" with -- myeloma --.

UNITED STATES PATENT AND TRADEMARK OFFICE
CERTIFICATE OF CORRECTION

PATENT NO.   : 6,852,710 B2
DATED        : February 8, 2005
INVENTOR(S)  : Rao et al.

It is certified that error appears in the above-identified patent and that said Letters Patent is hereby corrected as shown below:

Column 36 (cont'd),
Line 62, after "is" insert -- incorporated --.

Signed and Sealed this

Twenty-fourth Day of May, 2005

JON W. DUDAS
*Director of the United States Patent and Trademark Office*